US011964004B2

(12) United States Patent
Lin

(10) Patent No.: US 11,964,004 B2
(45) Date of Patent: Apr. 23, 2024

(54) SHORT IN VIVO HALF-LIFE AND IN VIVO UNSTABLE RECOMBINANT MICROPLASMIN, PHARMACEUTICAL COMPOSITION COMPRISING THEREOF AND METHOD OF TREATING THROMBOEMBOLISM RELATED DISEASES INCLUDING ADMINISTRATION THEREOF

(71) Applicant: SHENZHEN BAY LABORATORY, Shenzhen (CN)

(72) Inventor: Xinli Henry Lin, Shenzhen (CN)

(73) Assignee: SHENZHEN BAY LABORATORY, Shenzhen (CN)

( * ) Notice: Subject to any disclaimer, the term of this patent is extended or adjusted under 35 U.S.C. 154(b) by 0 days.

(21) Appl. No.: 17/709,403

(22) Filed: Mar. 30, 2022

(65) Prior Publication Data

US 2022/0387564 A1 Dec. 8, 2022

Related U.S. Application Data

(60) Provisional application No. 63/169,196, filed on Mar. 31, 2021.

(51) Int. Cl.
*A61K 38/48* (2006.01)
*A61P 7/02* (2006.01)

(52) U.S. Cl.
CPC .............. *A61K 38/484* (2013.01); *A61P 7/02* (2018.01)

(58) Field of Classification Search
CPC ................................ A61K 38/484; A61P 7/02
See application file for complete search history.

(56) References Cited

U.S. PATENT DOCUMENTS

2010/0144622 A1* 6/2010 Lin ................ C12Y 304/21007 530/394
2020/0299329 A1 9/2020 Wu et al.

FOREIGN PATENT DOCUMENTS

CN 102154253 A 8/2011
CN 106609266 A 5/2017

OTHER PUBLICATIONS

Yang, D., Zhu, W., Wang, Y. et al. Selection of mutant μplasmin for amyloid-β cleavage in vivo. Sci Rep 10, 12117 (2020). https://doi.org/10.1038/s41598-020-69079-8 (Year: 2000).*
Kaur et al., "Site-specific PEGylation of micro-plasmin for improved thrombolytic therapy through engineering enhanced resistance against serpin mediated inhibition", PLoS One. May 29, 2019;14(5):e0217234. doi: 10.1371/journal.pone.0217234. (Year: 2019).*

* cited by examiner

*Primary Examiner* — Ruth A Davis

(57) ABSTRACT

The present disclosure provides is a short in vivo half-life and in vivo unstable recombinant microplasmin, wherein the recombinant microplasmin can be a mutant type and wild type and is expressed in a bacteria host, can be purified, or can be refolded and purified in case expressed as an insoluble inclusion body, producing an active thrombolytic agent. The present disclosure also provides the pharmaceutical composition comprising the recombinant microplasmin and method of treating thromboembolism related diseases including the administration of the pharmaceutical composition.

7 Claims, 26 Drawing Sheets

Specification includes a Sequence Listing.

Trypsin:α1PI (PDB: 1OPH)

Thermostability of *E. coli* and Yeast Expressed uPlg

| Number | substrate: S2403 | Vmax (U/mg) | Km (μmol $L^{-1}$) | Kcat ($s^{-1}$) | Kcat/Km ($μmol^{-1}$ L $s^{-1}$) |
|---|---|---|---|---|---|
| a | H-uPlm | 31.34±0.81 | 648.3±65.34 | 1.0996 ±0.0284 | 0.00170 |
| b | M-uPlm | 24.97±0.49 | 237.3±19.27 | 0.8761 ±0.0172 | 0.00369 |
| c | H-A-uPlm | 31.73±1.20 | 527.4±73.73 | 1.1133 ±0.0421 | 0.00211 |
| d | H-uPlg | 5.252±0.14 | 338.2±41.19 | 0.1843± 0.0049 | 0.00054 |
| e | M-uPlg | 17.14±0.39 | 189.4±23.25 | 0.6014 ±0.0137 | 0.00318 |
| f | H-A-uPlg | 3.417±0.089 | 192.5±22.33 | 0.1199 ±0.0031 | 0.00062 |
| g | H-Yeast-uPlg | 24.86±0.59 | 418.4±56.55 | 0.8723 ±0.0207 | 0.00209 |
| i | M-Yeast-uPlg | 22.77±0.39 | 158.8±13.21 | 0.7989 ±0.0137 | 0.00503 |

```
 64 atggaacataaggaagtggttcttctacttcttttatttctgaaa
    M  E  H  K  E  V  V  L  L  L  L  L  F  L  K^-5
109 tcaggtcaaggagagcctctggatgactatgtgaatacccagggg
    S  G  Q  G^-1 E^1 P  L  D  D  Y  V  N  T  Q  G^11
154 gcttcactgttcagtgtcactaagaagcagctgggagcaggaagt
    A  S  L  F  S  V  T  K  K  Q  L  G  A  G  S^26
199 atagaagaatgtgcagcaaaatgtgaggaggacgaagaattcacc
    I  E  E  C  A  A  K  C  E  E  D  E  E  F  T^41
244 tgcagggcattccaatatcacagtaaagagcaacaatgtgtgata
    C  R  A  F  Q  Y  H  S  K  E  Q  Q  C  V  I^56
289 atggctgaaaacaggaagtcctccataatcattaggatgagagat
    M  A  E  N  R  K  S  S  I  I  I  R  M  R  D^71
334 gtagttttatttgaaaagaaagtgtatctctcagagtgcaagact
    V  V  L  F  E  K  K  V  Y  L  S  E  C  K  T^86
379 gggaatggaaagaactacagagggacgatgtccaaaacaaaaaat
    G  N  G  K  N  Y  R  G  T  M  S  K  T  K  N^101
424 ggcatcacctgtcaaaaatggagttccacttctccccacagacct
    G  I  T  C  Q  K  W  S  S  T  S  P  H  R  P^116
469 agattctcacctgctacacacccctcagagggactggaggagaac
    R  F  S  P  A  T  H  P  S  E  G  L  E  E  N^131
514 tactgcaggaatccagacaacgatccgcaggggccctggtgctat
    Y  C  R  N  P  D  N  D  P  Q  G  P  W  C  Y^146
559 actactgatccagaaaagagatatgactactgcgacattcttgag
    T  T  D  P  E  K  R  Y  D  Y  C  D  I  L  E^161
604 tgtgaagaggaatgtatgcattgcagtggagaaaactatgacggc
    C  E  E  E  C  M  H  C  S  G  E  N  Y  D  G^176
649 aaaatttccaagaccatgtctggactggaatgccaggcctgggac
    K  I  S  K  T  M  S  G  L  E  C  Q  A  W  D^191
694 tctcagagcccacacgctcatggatacattccttccaaatttcca
    S  Q  S  P  H  A  H  G  Y  I  P  S  K  F  P^206
739 aacaagaacctgaagaagaattactgtcgtaaccccgatagggag
    N  K  N  L  K  K  N  Y  C  R  N  P  D  R  E^221
784 ctgcggccttggtgtttcaccaccgaccccaacaagcgctgggaa
    L  R  P  W  C  F  T  T  D  P  N  K  R  W  E^236
829 ctttgtgacatccccccgctgcacaacacctccaccatcttctggt
    L  C  D  I  P  R  C  T  T  P  P  P  S  S  G^251
874 cccacctaccagtgtctgaagggaacaggtgaaaactatcgcggg
    P  T  Y  Q  C  L  K  G  T  G  E  N  Y  R  G^266
919 aatgtggctgttaccgtgtccgggcacacctgtcagcactggagt
    N  V  A  V  T  V  S  G  H  T  C  Q  H  W  S^281
964 gcacagacccctcacacacataacaggacaccagaaaacttcccc
    A  Q  T  P  H  T  H  N  R  T  P  E  N  F  P^296
```

Figure 23(1)

1009 tgcaaaaatttggatgaaaactactgccgcaatcctgacggaaaa
C K N L D E N Y C R N P D G K$^{311}$ 1054 agggccccatggtgccatacaaccaacagccaagtgcggtgggag
R A P W C H T T N S Q V R W E$^{326}$ 1099 tactgtaagataccgtcctgtgactcctccccagtatccacggaa
Y C K I P S C D S S P V S T E$^{341}$ 1144 caattggctcccacagcaccacctgagctaacccctgtggtccag
Q L A P T A P P E L T P V V Q$^{356}$ 1189 gactgctaccatggtgatggacagagctaccgaggcacatcctcc
D C Y H G D G Q S Y R G T S S$^{371}$ 1234 accaccaccacaggaaagaagtgtcagtcttggtcatctatgaca
T T T T G K K C Q S W S S M T$^{386}$ 1279 ccacaccggcaccagaagaccccagaaaactacccaaatgctggc
P H R H Q K T P E N Y P N A G$^{401}$ 1324 ctgacaatgaactactgcaggaatccagatgccgataaaggcccc
L T M N Y C R N P D A D K G P$^{416}$ 1369 tggtgttttaccacagaccccagcgtcaggtgggagtactgcaac
W C F T T D P S V R W E Y C N$^{431}$ 1414 ctgaaaaaatgctcaggaacagaagcgagtgttgtagcacctccg
L K K C S G T E A$^{440}$S V V A P P$^{446}$ 1459 cctgttgtcctgcttccagatgtagagactccttccgaagaagac
P V V L L P D V E T P S E E D$^{461}$ 1504 tgtatgtttgggaatgggaaaggataccgaggcaagagggcgacc
C M F G N G K G Y R G K R A T$^{476}$ 1549 actgttactgggacgccatgccaggactgggctgcccaggagccc
T V T G T P C Q D W A A Q E P$^{491}$ 1594 catagacacagcattttcactccagagacaaatccacgggcgggt
H R H S I F T P E T N P R A G$^{506}$ 1639 ctggaaaaaaattactgccgtaaccctgatggtgatgtaggtggt
L E K N Y C R N P D G D V G G$^{521}$ 1684 ccctggtgctacacgacaaatccaagaaaactttacgactactgt
P W C Y T T N P R K L Y D Y C$^{536}$ 1729 gatgtccctcagtgtgcggccccttcatttgattgtgggaagcct
D V P Q C A$^{542}$A P S F D C G K P$^{551}$

1774 caagtggagccgaagaaatgtcctggaagggttgtaggggggtgt
Q V E P K K C P G R$^{561}$V$^{562}$V G G C$^{566}$

1819 gtggcccacccacattcctggccctggcaagtcagtcttagaaca
V A H P H S W P W Q V S L R T$^{581}$

1864 aggtttggaatgcacttctgtggaggcaccttgatatccccagag
R F G M H F$^{587}$C G G T L I S P E$^{596}$

1909 tgggtgttgactgctgcccactgcttggagaagtccccaaggcct
W V L T A A H C L E K S P R P$^{611}$

Figure 23(2)

1954 tcatcctacaaggtcatcctgggtgcacaccaagaagtgaatctc
S S Y K V I L G A H Q E V N L[626]

1999 gaaccgcatgttcaggaaatagaagtgtctaggctgttcttggag
E P H V Q E I E V S R L F L E[641]

2044 cccacacgaaaagatattgccttgctaaagctaagcagtcctgcc
P T R K D I A L L K L S S P A[656]

2089 gtcatcactgacaaagtaatcccagcttgtctgccatccccaaat
V I T D K V I P A C L P S P N[671]

2134 tatgtggtcgctgaccggaccgaatgtttcatcactggctgggga
Y V V A D R T E C F I T G W G[686]

2179 gaaacccaaggtacttttggagctggccttctcaaggaagcccag
E T Q G T F G A G L L K E A Q[701]

2224 ctccctgtgattgagaataaagtgtgcaatcgctatgagtttctg
L P V I E N K V C N R Y E F L[716]

2269 aatggaagagtccaatccaccgaactctgtgctgggcatttggcc
N G R V Q S T E L C A G H L A[731]

2314 ggaggcactgacagttgccagggtgacagtggaggtcctctggtt
G G T D S C Q G D S G G P L V[746]

2359 tgcttcgagaaggacaaatacattttacaaggagtcacttcttgg
C F E K D K Y I L Q G V T S W[761]

2404 ggtcttggctgtgcacgccccaataagcctggtgtctatgttcgt
G L G C A R P N K P G V Y V R[776]

2449 gtttcaaggtttgttacttggattgagggagtgatgagaaataat
V S R F V T W I E G V M R N N[791]

2494 taa 2496

Figure 23(3)

1729 gatgtccctcagtgtgcggccccttcatttgattgtgggaagcct
D V P Q C A$^{542}$A P S F D C G K P$^{551}$ 1774 caagtggagccgaagaaatgtcctggaagggttgtagggggtgt
Q V E P K K C P G R V V G G C$^{566}$ 1819 gtggcccacccacattcctggccctggcaagtcagtcttagaaca
V A H P H S W P W Q V S L R T$^{581}$ Loop3

1864 aggtttggaatgcacttctgtggaggcaccttgatatccccagag
R F G M H F C G G T L I S P E$^{596}$ 1909 tgggtgttgactgctgcccactgcttggagaagtccccaaggcct
W V L T A A H$^{603}$C L$^{605}$E K S P R P$^{611}$ Loop 2

1954 tcatcctacaaggtcatcctgggtgcacaccaagaagtgaatctc
S S Y K V I L G A H Q E V N L$^{626}$ 1999 gaaccgcatgttcaggaaatagaagtgtctaggctgttcttggag
E P H V Q E I E V S R L F L E$^{641}$ Loop 1

2044 cccacacgaaaagatattgccttgctaaagctaagcagtcctgcc
P T R K D$^{646}$I A L L K L S S P A$^{656}$ 2089 gtcatcactgacaaagtaatcccagcttgtctgccatccccaaat
V I T D K V I P A C L P S P N$^{671}$ 2134 tatgtggtcgctgaccggaccgaatgtttcatcactggctgggga
Y V V A D R T E C F I T G W G$^{686}$ 2179 gaaacccaaggtactttggagctggccttctcaaggaagcccag
E T Q G T F G A G L L K E A Q$^{701}$ 2224 ctccctgtgattgagaataaagtgtgcaatcgctatgagtttctg
L P V I E N K V C N R Y E F L$^{716}$ 2269 aatggaagagtccaatccaccgaactctgtgctgggcatttggcc
N$^{717}$G R V Q S T E L C A G H L A$^{731}$ Loop 6

2314 ggaggcactgacagttgccagggtgacagtggaggtcctctggtt
G G T D S C Q$^{738}$G D S$^{741}$G G P L V$^{746}$ Loop 4

2359 tgcttcgagaaggacaaatacatttacaaggagtcacttcttgg
C F E K D K Y I L Q G V T S$^{760}$W$^{761}$ Loop 5

2404 ggtcttggctgtgcacgccccaataagcctggtgtctatgttcgt
G L G C A R P N K P G V Y V R$^{776}$ 2449 gtttcaaggtttgttacttggattgagggagtgatgagaaataat
V S R F V T W I E G V M R N N$^{791}$ 2494 taa 2496
*

Figure 24

```
SEQUENCE LISTING

<160> NUMBER OF SEQ ID NOS: 16

<210> SEQ ID NO 1
<211> LENGTH: 2759
<212> TYPE: DNA
<213> ORGANISM: Homo sapiens
<220> FEATURE:
<221> NAME/KEY: misc_feature
<222> LOCATION: (1)..(2759)
<223> OTHER INFORMATION: cDNA sequence of Native Human plg

<400> SEQUENCE: 1

atgtaagtca acaacatcct gggattggga cccactttct gggcactgct ggccagtccc     60

aaaatggaac ataaggaagt ggttcttcta cttcttttat ttctgaaatc aggtcaagga    120

gagcctctgg atgactatgt gaatacccag ggggcttcac tgttcagtgt cactaagaag    180

cagctgggag caggaagtat agaagaatgt gcagcaaaat gtgaggagga cgaagaattc    240

acctgcaggg cattccaata tcacagtaaa gagcaacaat gtgtgataat ggctgaaaac    300

aggaagtcct ccataatcat taggatgaga gatgtagttt tatttgaaaa gaaagtgtat    360

ctctcagagt gcaagactgg gaatggaaag aactacagag ggacgatgtc caaaacaaaa    420

aatggcatca cctgtcaaaa atggagttcc acttctcccc acagacctag attctcacct    480

gctacacacc cctcagaggg actggaggag aactactgca ggaatccaga caacgatccg    540

caggggccct ggtgctatac tactgatcca gaaaagagat atgactactg cgacattctt    600

gagtgtgaag aggaatgtat gcattgcagt ggagaaaact atgacggcaa aatttccaag    660

accatgtctg gactggaatg ccaggcctgg gactctcaga gcccacacgc tcatggatac    720

attccttcca aatttccaaa caagaacctg aagaagaatt actgtcgtaa ccccgatagg    780

gagctgcggc cttggtgttt caccaccgac cccaacaagc gctgggaact ttgtgacatc    840

ccccgctgca caacacctcc accatcttct ggtcccacct accagtgtct gaagggaaca    900
```

```
ggtgaaaact atcgcgggaa tgtggctgtt accgtgtccg ggcacacctg tcagcactgg    960

agtgcacaga cccctcacac acataacagg acaccagaaa acttcccctg caaaaatttg   1020

gatgaaaact actgccgcaa tcctgacgga aaaagggccc catggtgcca tacaaccaac   1080

agccaagtgc ggtgggagta ctgtaagata ccgtcctgtg actcctcccc agtatccacg   1140

gaacaattgg ctcccacagc accacctgag ctaacccctg tggtccagga ctgctaccat   1200

ggtgatggac agagctaccg aggcacatcc tccaccacca ccacaggaaa gaagtgtcag   1260

tcttggtcat ctatgacacc acaccggcac cagaagaccc cagaaaacta cccaaatgct   1320

ggcctgacaa tgaactactg caggaatcca gatgccgata aaggcccctg gtgttttacc   1380

acagacccca gcgtcaggtg ggagtactgc aacctgaaaa aatgctcagg aacagaagcg   1440

agtgttgtag cacctccgcc tgttgtcctg cttccagatg tagagactcc ttccgaagaa   1500

gactgtatgt ttgggaatgg gaaaggatac cgaggcaaga gggcgaccac tgttactggg   1560

acgccatgcc aggactgggc tgcccaggag ccccatagac acagcatttt cactccagag   1620

acaaatccac gggcgggtct ggaaaaaaat tactgccgta accctgatgg tgatgtaggt   1680

ggtccctggt gctacacgac aaatccaaga aaactttacg actactgtga tgtccctcag   1740

tgtgcggccc cttcatttga ttgtgggaag cctcaagtgg agccgaagaa atgtcctgga   1800

agggttgtag gggggtgtgt ggcccaccca cattcctggc cctggcaagt cagtcttaga   1860

acaaggtttg gaatgcactt ctgtggaggc accttgatat ccccagagtg ggtgttgact   1920

gctgcccact gcttggagaa gtccccaagg ccttcatcct acaaggtcat cctgggtgca   1980

caccaagaag tgaatctcga accgcatgtt caggaaatag aagtgtctag gctgttcttg   2040

gagcccacac gaaaagatat tgccttgcta aagctaagca gtcctgccgt catcactgac   2100

aaagtaatcc cagcttgtct gccatcccca aattatgtgg tcgctgaccg gaccgaatgt   2160

ttcatcactg gctggggaga aacccaaggt acttttggag ctggccttct caaggaagcc   2220

cagctccctg tgattgagaa taaagtgtgc aatcgctatg agtttctgaa tggaagagtc   2280

caatccaccg aactctgtgc tgggcatttg gccggaggca ctgacagttg ccagggtgac   2340

agtggaggtc ctctggtttg cttcgagaag gacaaataca ttttacaagg agtcacttct   2400

tggggtcttg gctgtgcacg ccccaataag cctggtgtct atgttcgtgt ttcaaggttt   2460

gttacttgga ttgagggagt gatgagaaat aattaattgg acgggagaca gagtgacgca   2520

ctgactcacc tagaggctgg aacgtgggta gggatttagc atgctggaaa taactggcag   2580

taatcaaacg aagacactgt ccccagctac cagctacgcc aaacctcggc atttttttgtg   2640

ttattttctg actgctggat tctgtagtaa ggtgacatag ctatgacatt tgttaaaaat   2700

aaactctgta cttaactttg atttgagtaa attttggttt tggtcttcaa aaaaaaaaa    2759


<210> SEQ ID NO 2
<211> LENGTH: 810
<212> TYPE: PRT
<213> ORGANISM: Homo sapiens
<220> FEATURE:
<221> NAME/KEY: MISC_FEATURE
<222> LOCATION: (1)..(810)
<223> OTHER INFORMATION: amino acid sequence of Native Human plg

<400> SEQUENCE: 2

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30
```

```
Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445
```

```
Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810
```

<210> SEQ ID NO 3
<211> LENGTH: 1059
<212> TYPE: DNA
<213> ORGANISM: Homo sapiens
<220> FEATURE:
<221> NAME/KEY: misc_feature
<222> LOCATION: (1)..(1059)
<223> OTHER INFORMATION: cDNA sequence of mimiPlg in Native Human plg

<400> SEQUENCE: 3

```
gcgagtgttg tagcacctcc gcctgttgtc ctgcttccag atgtagagac tccttccgaa     60
gaagactgta tgtttgggaa tgggaaagga taccgaggca agagggcgac cactgttact    120
gggacgccat gccaggactg ggctgcccag gagccccata gacacagcat tttcactcca    180
gagacaaatc cacgggcggg tctggaaaaa aattactgcc gtaaccctga tggtgatgta    240
ggtggtccct ggtgctacac gacaaatcca agaaaacttt acgactactg tgatgtccct    300
cagtgtgcgg cccttcatt tgattgtggg aagcctcaag tggagccgaa gaaatgtcct    360
ggaagggttg tagggggggtg tgtggcccac ccacattcct ggccctggca agtcagtctt    420
agaacaaggt ttggaatgca cttctgtgga ggcaccttga tatccccaga gtgggtgttg    480
actgctgccc actgcttgga gaagtcccca aggccttcat cctacaaggt catcctgggt    540
gcacaccaag aagtgaatct cgaaccgcat gttcaggaaa tagaagtgtc taggctgttc    600
ttggagccca cacgaaaaga tattgccttg ctaaagctaa gcagtcctgc cgtcatcact    660
gacaaagtaa tcccagcttg tctgccatcc ccaaattatg tggtcgctga ccggaccgaa    720
tgtttcatca ctggctgggg agaaacccaa ggtacttttg gagctggcct tctcaaggaa    780
gcccagctcc ctgtgattga gaataaagtg tgcaatcgct atgagtttct gaatggaaga    840
gtccaatcca ccgaactctg tgctgggcat ttggccggag gcactgacag ttgccagggt    900
gacagtggag gtcctctggt ttgcttcgag aaggacaaat acattttaca aggagtcact    960
tcttggggtc ttggctgtgc acgccccaat aagcctggtg tctatgttcg tgtttcaagg   1020
tttgttactt ggattgaggg agtgatgaga aataattaa                          1059
```

<210> SEQ ID NO 4
<211> LENGTH: 352
<212> TYPE: PRT
<213> ORGANISM: Homo sapiens
<220> FEATURE:
<221> NAME/KEY: MISC_FEATURE
<222> LOCATION: (1)..(352)
<223> OTHER INFORMATION: amino acid sequence of miniPlg in Native Human plg

<400> SEQUENCE: 4

```
Ala Ser Val Val Ala Pro Pro Pro Val Val Leu Leu Pro Asp Val Glu
1               5                   10                  15

Thr Pro Ser Glu Glu Asp Cys Met Phe Gly Asn Gly Lys Gly Tyr Arg
            20                  25                  30

Gly Lys Arg Ala Thr Thr Val Thr Gly Thr Pro Cys Gln Asp Trp Ala
        35                  40                  45

Ala Gln Glu Pro His Arg His Ser Ile Phe Thr Pro Glu Thr Asn Pro
    50                  55                  60

Arg Ala Gly Leu Glu Lys Asn Tyr Cys Arg Asn Pro Asp Gly Asp Val
65                  70                  75                  80

Gly Gly Pro Trp Cys Tyr Thr Thr Asn Pro Arg Lys Leu Tyr Asp Tyr
                85                  90                  95

Cys Asp Val Pro Gln Cys Ala Ala Pro Ser Phe Asp Cys Gly Lys Pro
            100                 105                 110

Gln Val Glu Pro Lys Lys Cys Pro Gly Arg Val Val Gly Gly Cys Val
        115                 120                 125

Ala His Pro His Ser Trp Pro Trp Gln Val Ser Leu Arg Thr Arg Phe
    130                 135                 140

Gly Met His Phe Cys Gly Gly Thr Leu Ile Ser Pro Glu Trp Val Leu
```

```
145                 150                 155                 160

Thr Ala Ala His Cys Leu Glu Lys Ser Pro Arg Pro Ser Ser Tyr Lys
                165                 170                 175

Val Ile Leu Gly Ala His Gln Glu Val Asn Leu Glu Pro His Val Gln
            180                 185                 190

Glu Ile Glu Val Ser Arg Leu Phe Leu Glu Pro Thr Arg Lys Asp Ile
        195                 200                 205

Ala Leu Leu Lys Leu Ser Ser Pro Ala Val Ile Thr Asp Lys Val Ile
    210                 215                 220

Pro Ala Cys Leu Pro Ser Pro Asn Tyr Val Val Ala Asp Arg Thr Glu
225                 230                 235                 240

Cys Phe Ile Thr Gly Trp Gly Glu Thr Gln Gly Thr Phe Gly Ala Gly
                245                 250                 255

Leu Leu Lys Glu Ala Gln Leu Pro Val Ile Glu Asn Lys Val Cys Asn
            260                 265                 270

Arg Tyr Glu Phe Leu Asn Gly Arg Val Gln Ser Thr Glu Leu Cys Ala
        275                 280                 285

Gly His Leu Ala Gly Gly Thr Asp Ser Cys Gln Gly Asp Ser Gly Gly
    290                 295                 300

Pro Leu Val Cys Phe Glu Lys Asp Lys Tyr Ile Leu Gln Gly Val Thr
305                 310                 315                 320

Ser Trp Gly Leu Gly Cys Ala Arg Pro Asn Lys Pro Gly Val Tyr Val
                325                 330                 335

Arg Val Ser Arg Phe Val Thr Trp Ile Glu Gly Val Met Arg Asn Asn
            340                 345                 350
```

<210> SEQ ID NO 5
<211> LENGTH: 753
<212> TYPE: DNA
<213> ORGANISM: Homo sapiens
<220> FEATURE:
<221> NAME/KEY: misc_feature
<222> LOCATION: (1)..(753)
<223> OTHER INFORMATION: cDNA sequence of microPlg in Native Human plg

<400> SEQUENCE: 5

```
gcggcccctt catttgattg tgggaagcct caagtggagc cgaagaaatg tcctggaagg     60

gttgtagggg ggtgtgtggc ccacccacat tcctggccct ggcaagtcag tcttagaaca    120

aggtttggaa tgcacttctg tggaggcacc ttgatatccc cagagtgggt gttgactgct    180

gcccactgct tggagaagtc cccaaggcct tcatcctaca aggtcatcct gggtgcacac    240

caagaagtga atctcgaacc gcatgttcag gaaatagaag tgtctaggct gttcttggag    300

cccacacgaa aagatattgc cttgctaaag ctaagcagtc ctgccgtcat cactgacaaa    360

gtaatcccag cttgtctgcc atccccaaat tatgtggtcg ctgaccggac cgaatgtttc    420

atcactggct ggggagaaac ccaaggtact tttggagctg gccttctcaa ggaagcccag    480

ctccctgtga ttgagaataa agtgtgcaat cgctatgagt ttctgaatgg aagagtccaa    540

tccaccgaac tctgtgctgg gcatttggcc ggaggcactg acagttgcca gggtgacagt    600

ggaggtcctc tggtttgctt cgagaaggac aaatacattt tacaaggagt cacttcttgg    660

ggtcttggct gtgcacgccc caataagcct ggtgtctatg ttcgtgtttc aaggtttgtt    720

acttggattg agggagtgat gagaaataat taa                                 753
```

<210> SEQ ID NO 6
<211> LENGTH: 250

```
<212> TYPE: PRT
<213> ORGANISM: Homo sapiens
<220> FEATURE:
<221> NAME/KEY: MISC_FEATURE
<222> LOCATION: (1)..(250)
<223> OTHER INFORMATION: amino acid sequence of microPlg in Native Human
      plg

<400> SEQUENCE: 6

Ala Ala Pro Ser Phe Asp Cys Gly Lys Pro Gln Val Glu Pro Lys Lys
1               5                   10                  15

Cys Pro Gly Arg Val Val Gly Gly Cys Val Ala His Pro His Ser Trp
            20                  25                  30

Pro Trp Gln Val Ser Leu Arg Thr Arg Phe Gly Met His Phe Cys Gly
        35                  40                  45

Gly Thr Leu Ile Ser Pro Glu Trp Val Leu Thr Ala Ala His Cys Leu
    50                  55                  60

Glu Lys Ser Pro Arg Pro Ser Ser Tyr Lys Val Ile Leu Gly Ala His
65                  70                  75                  80

Gln Glu Val Asn Leu Glu Pro His Val Gln Glu Ile Glu Val Ser Arg
                85                  90                  95

Leu Phe Leu Glu Pro Thr Arg Lys Asp Ile Ala Leu Leu Lys Leu Ser
            100                 105                 110

Ser Pro Ala Val Ile Thr Asp Lys Val Ile Pro Ala Cys Leu Pro Ser
        115                 120                 125

Pro Asn Tyr Val Val Ala Asp Arg Thr Glu Cys Phe Ile Thr Gly Trp
    130                 135                 140

Gly Glu Thr Gln Gly Thr Phe Gly Ala Gly Leu Leu Lys Glu Ala Gln
145                 150                 155                 160

Leu Pro Val Ile Glu Asn Lys Val Cys Asn Arg Tyr Glu Phe Leu Asn
                165                 170                 175

Gly Arg Val Gln Ser Thr Glu Leu Cys Ala Gly His Leu Ala Gly Gly
            180                 185                 190

Thr Asp Ser Cys Gln Gly Asp Ser Gly Gly Pro Leu Val Cys Phe Glu
        195                 200                 205

Lys Asp Lys Tyr Ile Leu Gln Gly Val Thr Ser Trp Gly Leu Gly Cys
    210                 215                 220

Ala Arg Pro Asn Lys Pro Gly Val Tyr Val Arg Val Ser Arg Phe Val
225                 230                 235                 240

Thr Trp Ile Glu Gly Val Met Arg Asn Asn
                245                 250


<210> SEQ ID NO 7
<211> LENGTH: 753
<212> TYPE: DNA
<213> ORGANISM: Escherichia coli
<220> FEATURE:
<221> NAME/KEY: CDS
<222> LOCATION: (298)..(312)
<223> OTHER INFORMATION: cDNA sequence of Loop 1 in mutative Human
      microplg

<400> SEQUENCE: 7

gcggcccctt catttgattg tgggaagcct caagtggagc cgaagaaatg tcctggaagg      60

gttgtagggg ggtgtgtggc ccacccacat tcctggccct ggcaagtcag tcttagaaca     120

aggtttggaa tgcacttctg tggaggcacc ttgatatccc cagagtgggt gttgactgct     180

gcccactgct tggagaagtc cccaaggcct tcatcctaca aggtcatcct gggtgcacac     240
```

```
caagaagtga atctcgaacc gcatgttcag gaaatagaag tgtctaggct gttcttg       297

gag ccc aca cga aaa gatattgcct tgctaaagct aagcagtcct gccgtcatca      352
Glu Pro Thr Arg Lys
1               5

ctgacaaagt aatcccagct tgtctgccat ccccaaatta tgtggtcgct gaccggaccg    412

aatgtttcat cactggctgg ggagaaaccc aaggtacttt tggagctggc cttctcaagg    472

aagcccagct ccctgtgatt gagaataaag tgtgcaatcg ctatgagttt ctgaatggaa    532

gagtccaatc caccgaactc tgtgctgggc atttggccgg aggcactgac agttgccagg    592

gtgacagtgg aggtcctctg gtttgcttcg agaaggacaa atacatttta caaggagtca    652

cttcttgggg tcttggctgt gcacgcccca ataagcctgg tgtctatgtt cgtgtttcaa    712

ggtttgttac ttggattgag ggagtgatga gaaataatta a                        753


<210> SEQ ID NO 8
<211> LENGTH: 5
<212> TYPE: PRT
<213> ORGANISM: Escherichia coli

<400> SEQUENCE: 8

Glu Pro Thr Arg Lys
1               5


<210> SEQ ID NO 9
<211> LENGTH: 753
<212> TYPE: DNA
<213> ORGANISM: Escherichia coli
<220> FEATURE:
<221> NAME/KEY: CDS
<222> LOCATION: (190)..(213)
<223> OTHER INFORMATION: cDNA sequence of Loop 2 in mutative Human
      microplg

<400> SEQUENCE: 9

gcggcccctt catttgattg tgggaagcct caagtggagc cgaagaaatg tcctggaagg     60

gttgtagggg ggtgtgtggc ccacccacat tcctggccct ggcaagtcag tcttagaaca    120

aggtttggaa tgcacttctg tggaggcacc ttgatatccc cagagtgggt gttgactgct    180

gcccactgc ttg gag aag tcc cca agg cct tca tcctacaagg tcatcctggg      233
          Leu Glu Lys Ser Pro Arg Pro Ser
          1               5

tgcacaccaa gaagtgaatc tcgaaccgca tgttcaggaa atagaagtgt ctaggctgtt    293

cttggagccc acacgaaaag atattgcctt gctaaagcta agcagtcctg ccgtcatcac    353

tgacaaagta atcccagctt gtctgccatc cccaaattat gtggtcgctg accggaccga    413

atgtttcatc actggctggg gagaaaccca aggtactttt ggagctggcc ttctcaagga    473

agcccagctc cctgtgattg agaataaagt gtgcaatcgc tatgagtttc tgaatggaag    533

agtccaatcc accgaactct gtgctgggca tttggccgga ggcactgaca gttgccaggg    593

tgacagtgga ggtcctctgg tttgcttcga gaaggacaaa tacattttac aaggagtcac    653

ttcttggggt cttggctgtg cacgccccaa taagcctggt gtctatgttc gtgtttcaag    713

gtttgttact tggattgagg gagtgatgag aaataattaa                          753


<210> SEQ ID NO 10
<211> LENGTH: 8
<212> TYPE: PRT
<213> ORGANISM: Escherichia coli

<400> SEQUENCE: 10
```

```
Leu Glu Lys Ser Pro Arg Pro Ser
1               5


<210> SEQ ID NO 11
<211> LENGTH: 753
<212> TYPE: DNA
<213> ORGANISM: Escherichia coli
<220> FEATURE:
<221> NAME/KEY: CDS
<222> LOCATION: (118)..(132)
<223> OTHER INFORMATION: cDNA sequence of Loop 3 in mutative Human
      microplg

<400> SEQUENCE: 11

gcggcccctt catttgattg tgggaagcct caagtggagc cgaagaaatg tcctggaagg      60

gttgtagggg ggtgtgtggc ccacccacat tcctggccct ggcaagtcag tcttaga        117

aca agg ttt gga atg cacttctgtg gaggcacctt gatatcccca gagtgggtgt       172
Thr Arg Phe Gly Met
1               5

tgactgctgc ccactgcttg gagaagtccc caaggccttc atcctacaag gtcatcctgg     232

gtgcacacca agaagtgaat ctcgaaccgc atgttcagga aatagaagtg tctaggctgt     292

tcttggagcc cacacgaaaa gatattgcct tgctaaagct aagcagtcct gccgtcatca     352

ctgacaaagt aatcccagct tgtctgccat ccccaaatta tgtggtcgct gaccggaccg     412

aatgtttcat cactggctgg ggagaaaccc aaggtacttt tggagctggc cttctcaagg     472

aagcccagct ccctgtgatt gagaataaag tgtgcaatcg ctatgagttt ctgaatggaa     532

gagtccaatc caccgaactc tgtgctgggc atttggccgg aggcactgac agttgccagg     592

gtgacagtgg aggtcctctg gtttgcttcg agaaggacaa atacatttta caaggagtca     652

cttcttgggg tcttggctgt gcacgcccca ataagcctgg tgtctatgtt cgtgtttcaa     712

ggtttgttac ttggattgag ggagtgatga gaaataatta a                         753


<210> SEQ ID NO 12
<211> LENGTH: 5
<212> TYPE: PRT
<213> ORGANISM: Escherichia coli

<400> SEQUENCE: 12

Thr Arg Phe Gly Met
1               5


<210> SEQ ID NO 13
<211> LENGTH: 753
<212> TYPE: DNA
<213> ORGANISM: Escherichia coli
<220> FEATURE:
<221> NAME/KEY: CDS
<222> LOCATION: (655)..(669)
<223> OTHER INFORMATION: cDNA sequence of Loop 5 in mutative Human
      microplg

<400> SEQUENCE: 13

gcggcccctt catttgattg tgggaagcct caagtggagc cgaagaaatg tcctggaagg      60

gttgtagggg ggtgtgtggc ccacccacat tcctggccct ggcaagtcag tcttagaaca     120

aggtttggaa tgcacttctg tggaggcacc ttgatatccc cagagtgggt gttgactgct     180

gcccactgct tggagaagtc cccaaggcct tcatcctaca aggtcatcct gggtgcacac     240

caagaagtga atctcgaacc gcatgttcag gaaatagaag tgtctaggct gttcttggag     300
```

```
cccacacgaa aagatattgc cttgctaaag ctaagcagtc ctgccgtcat cactgacaaa    360

gtaatcccag cttgtctgcc atccccaaat tatgtggtcg ctgaccggac cgaatgtttc    420

atcactggct ggggagaaac ccaaggtact tttggagctg gccttctcaa ggaagcccag    480

ctccctgtga ttgagaataa agtgtgcaat cgctatgagt ttctgaatgg aagagtccaa    540

tccaccgaac tctgtgctgg gcatttggcc ggaggcactg acagttgcca gggtgacagt    600

ggaggtcctc tggtttgctt cgagaaggac aaatacattt tacaaggagt cact tct      657
                                                            Ser
                                                            1

tgg ggt ctt ggc tgtgcacgcc ccaataagcc tggtgtctat gttcgtgttt          709
Trp Gly Leu Gly
            5

caaggtttgt tacttggatt gagggagtga tgagaaataa ttaa                     753


<210> SEQ ID NO 14
<211> LENGTH: 5
<212> TYPE: PRT
<213> ORGANISM: Escherichia coli

<400> SEQUENCE: 14

Ser Trp Gly Leu Gly
1               5


<210> SEQ ID NO 15
<211> LENGTH: 753
<212> TYPE: DNA
<213> ORGANISM: Escherichia coli
<220> FEATURE:
<221> NAME/KEY: CDS
<222> LOCATION: (526)..(549)
<223> OTHER INFORMATION: cDNA sequence of Loop 6 in mutative Human
      microplg

<400> SEQUENCE: 15

gcggcccctt catttgattg tgggaagcct caagtggagc cgaagaaatg tcctggaagg     60

gttgtagggg ggtgtgtggc ccacccacat tcctggccct ggcaagtcag tcttagaaca    120

aggtttggaa tgcacttctg tggaggcacc ttgatatccc cagagtgggt gttgactgct    180

gcccactgct tggagaagtc cccaaggcct tcatcctaca aggtcatcct gggtgcacac    240

caagaagtga atctcgaacc gcatgttcag gaaatagaag tgtctaggct gttcttggag    300

cccacacgaa aagatattgc cttgctaaag ctaagcagtc ctgccgtcat cactgacaaa    360

gtaatcccag cttgtctgcc atccccaaat tatgtggtcg ctgaccggac cgaatgtttc    420

atcactggct ggggagaaac ccaaggtact tttggagctg gccttctcaa ggaagcccag    480

ctccctgtga ttgagaataa agtgtgcaat cgctatgagt ttctg aat gga aga gtc    537
                                                  Asn Gly Arg Val
                                                  1

caa tcc acc gaa ctctgtgctg ggcatttggc cggaggcact gacagttgcc          589
Gln Ser Thr Glu
5

agggtgacag tggaggtcct ctggtttgct tcgagaagga caaatacatt ttacaaggag    649

tcacttcttg gggtcttggc tgtgcacgcc ccaataagcc tggtgtctat gttcgtgttt    709

caaggtttgt tacttggatt gagggagtga tgagaaataa ttaa                     753


<210> SEQ ID NO 16
<211> LENGTH: 8
<212> TYPE: PRT
<213> ORGANISM: Escherichia coli
```

-continued

<400> SEQUENCE: 16

```
Asn Gly Arg Val Gln Ser Thr Glu
1               5
```

SHORT IN VIVO HALF-LIFE AND IN VIVO UNSTABLE RECOMBINANT MICROPLASMIN, PHARMACEUTICAL COMPOSITION COMPRISING THEREOF AND METHOD OF TREATING THROMBOEMBOLISM RELATED DISEASES INCLUDING ADMINISTRATION THEREOF

CROSS-REFERENCE TO RELATED APPLICATION

This application claims the benefit of U.S. Provisional Application No. 63/169,196, filed Mar. 31, 2021 and titled "A NOVEL THERAPEUTIC METHOD OF USING SHORT IN VIVO HALF-LIFE AND UNSTABLE THROMBOLYTIC AGENTS", the contents of which are incorporated herein by reference in its entirety.

FIELD OF DISCLOSURE

The present application relates to the technical field of recombinant proteins and thrombolytic therapeutics for treating cardiovascular and other blood clotting caused diseases.

REFERENCE TO SEQUENCE LISTING

The Sequence Listing resubmitted concurrently herewith under 37 CFR § 1.821 in a computer readable form (CRF) via EFS-Web as file name SEQUENCE LISTING REVISED.txt is incorporated herein by reference. The electronic copy of the Sequence Listing was created on Aug. 2, 2022, with a file size of 26.5 bytes.

BACKGROUND

Nowadays, death caused by thrombotic diseases caused by disturbance of the hemostatic balance in case of pathogenic thromboembolism accounts for 51% of total global death, which is amount far beyond death caused by cancer. The intricate fibrinolytic network in the blood circulating system includes proenzyme plasminogen (Plg)/enzyme plasmin (Plm), urokinase-type plasminogen activator (uPA)/tissue-type plasminogen activator (tPA) and inhibitors such as Plg activator inhibitor (PAI), which binds to and inhibit tPA and uPA, and a2-antiplasmin (a2-AP), which binds to and inhibit Plm. In vivo, the pathogenic thrombi are dissolved into soluble components by the enzyme plasmin, a serine protease that is derived from the proenzyme plasminogen. Plg binds to both fibrin and fibrinogen, thereby incorporating into a clot as it is formed. Both urokinase-type plasminogen activator and tissue-type plasminogen activator are exquisitely specific serine proteases which convert Plg to Plm. The activation of the fibrinolytic system can be carried out through three pathways, namely the internal activation pathway, the external activation pathway and the exogenous activation pathway. The endogenous activation pathway is mainly initiated by the relevant factors of the endogenous coagulation system and it is the theoretical basis for secondary fibrinolysis. The external activation pathway is mainly the process of converting plasminogen into plasmin by tissue-type plasminogen activator and urokinase-type plasminogen activator. At the same time, t-PA and u-PA are inhibited by plasminogen activator inhibitor (PAI-1/2/3), which regulates fibrinolytic activity through activation and inhibition. This pathway is the theoretical basis of primary fibrinolysis. The exogenous activation pathway achieves the purpose of thrombolysis mainly by injecting fibrinolytic activators such as streptokinase, urokinase, and recombinant t-PA into the body to activate the fibrinolytic system. This pathway is the theoretical basis of thrombolytic therapy. Although there are many therapeutic developments toward Plg activation and modulation of Plm activities based on the internal activation pathway, and currently using the plasminogen activator drugs such as tPA as the first-line treatment based on the external activation pathway, the treatment using exogenous thrombolytic drug such as Plm-based direct thrombolytic drugs, however, has not been successful.

Plasminogen activators (PAs) have been dominated the thrombolytic therapy, but the bleeding side effects are inherent and cannot be solved easily. Besides genetic defects, Plg deficiency during PA treatment is also a serious medical problem, which can decrease or terminate the therapeutic efficacy. Unfortunately, there are currently no FDA-approved alternative drugs to PA treatment for conditions such as ischemic stroke, myocardial infarction, peripheral artery embolism, deep vein thrombosis, and other conditions caused by thromboembolism. For example, during thrombolytic therapy with high doses of tPA, uPA, or streptokinase (SK), there is a depletion of Plg that may terminate the efficiency of the thrombolytic drugs. On the other hand, it has been shown in animal models that the administration of Plg has restored the thrombolytic potential. In addition, decreased levels of Plg or Plm have been shown in several clinical conditions, including disseminated intravascular coagulation, sepsis, leukemia, hyaline membrane disease, liver disease, lung fibrosis, and Alzheimer's disease.

As a result, protein augmentation therapeutics with Plg and Plm based design may advance the field in many medical areas. Plm and μPlm did not result in bleeding at an extra-thrombus hemostatic stable plug far away from the site of infusion at the administered doses. tPA however, did cause bleeding at all concentrations at the extra-thrombus plug site. In addition, it has been shown that μPlm, which lacks the kringle domains of Plm and therefore does not possess the extra-fibrin binding specificity, is as effective as Plm at a similar pharmacological dose. However, as described above, in the serum, the activity of Plm is immediately neutralized by its principle inhibitor, α2-antiplasmin. Accordingly, one of the major hurdles in the application of Plm-based direct thrombolytic therapeutics is the decreased efficacy due to α2-AP inhibition. Therefore, in developing Plm-based therapeutics, it is desirable to design strategies to escape or overcome inhibition by α2-AP while being effective in dissolving disease-causing blood clots, but lost activity after therapeutic actions, avoiding bleeding side effects.

SUMMARY OF THE INVENTION

The present disclosure provides a short in vivo half-life and in vivo unstable recombinant microplasmin, wherein the recombinant microplasmin is expressed in a bacteria host, can be purified, or can be refolded and purified in case expressed as an insoluble inclusion body, producing an active thrombolytic agent.

In some embodiments, the in vivo half-life of the recombinant microplasmin is about 2.75 to about 28.5 minutes.

In some embodiments, the short in vivo half-life and in vivo unstable recombinant microplasmin includes wild-type, Gly739Ala, Arg582Ala, Met585Ala, Lys607Ala, Phe587Ala, Ser608Ala, Arg610Ala, Glu641Ala, and Pro642Ala.

In some embodiments, the recombinant microplasmin includes a wild type and a mutant type.

In some embodiments, the recombinant microplasmin includes a human and mouse microplasmin.

In some embodiments, the recombinant microplasmin is expressed and purified from an *E. coli* expression system.

In some embodiments, the recombinant microplasmin is selected to be biologically active in cleaving and detoxifying a pathogenic polypeptide or insoluble fibrin and is also resisting α2-antiplasmin inhibition.

In other aspects, the present disclosure provides a pharmaceutical composition comprising the above recombinant microplasmin as a thrombolytic agent, or a pharmaceutically acceptable dosage form thereof, or a pharmaceutically acceptable solvate of said compound or dosage form, and including a pharmaceutically acceptable excipient.

In some embodiments, the *E. coli* expressed insoluble recombinant microplasmin is refolded and purified into an active form for thrombolytic applications.

In yet other aspects, the present disclosure provides a method of treating thromboembolism related diseases including ischemic stroke, myocardial infarction, deep vein thrombosis, peripheral arterial occlusion, pulmonary embolism, and systemic blood clotting caused by various disease conditions such as SARS-CoV2 infection and sepsis, wherein the method includes the administration to a subject suffering therefrom a therapeutically effective amount of the above pharmaceutical composition, or a pharmaceutically acceptable dosage form thereof, or a pharmaceutically acceptable solvate of said compound or dosage form.

In some embodiments, the pharmaceutical composition is administrated by intravenous, catheter-directed local application, subcutaneous, submuscular, and aerosol routes.

Definitions

The term "in vivo half-life", as used herein, means the time it takes for the concentration of a drug in the blood or the amount of a drug in vivo to be decreased to its original half. The calculation formula of in vivo half-life (shown as t½) is: t½=0.693/k, wherein k is the elimination rate constant. The in vivo half-life of a drug can be calculated according to the above formula as long as the K value of a drug is calculated. For example, if the blood concentration of a drug 2 hours after the administration is 25% and the blood concentration 5 hours after administration is 19%, then the elimination rate constant of this drug, i.e. K=(Inco−Inc)/t=(In25−In19)/(5−2)=0.091 h. The half-life of this drug, i.e. t½=0.693/k=7.6 hours.

In the present disclosure, "in vivo half-life" for plasmin-based therapeutics has two different definitions. The first definition is the in vivo enzyme activity half-life. Once in the blood, at low concentration (<1 μM, which is the serum concentration of α2-AP), Plm is immediately neutralized by its principle inhibitor α2-AP, and has an activity half-life of only 0.2 seconds, while μPlm has a relatively longer activity plasma half-life of about 4 seconds. The second definition is the inherent structural stability of the protein per se in the blood. For example, recombinant μPlm refolded from *E. coli* inclusion bodies is stable in the controlled buffer and temperature of laboratory conditions, but the protein itself becomes unstable once injected into the blood of a live mouse, with a structural half-life as short as 2.75 minutes; on the other hand, the in vivo structural half-life of native Plg and Plm can be as long as 2-4 days. In the "hit and die" strategy, the inventor of the present disclosure used the second definition when describing in vivo stability and half-life. In the present disclosure, the "quick death" of the μPlm therapeutics is not resulting from the inhibition of protease inhibitors present in the serum, but is a situation in which at high concentration (>1 μM), after neutralizing all of the inhibitor activities and dissolving the targeting thrombi, the loss of the remaining enzyme activity from the structural disintegration of the recombinant enzyme itself.

The term "in vivo unstable", as used herein, means that polypeptide or protein molecules form new "inactive" chemical entities through the formation and breaking of covalent bonds or have physical transformation of higher-order structures without covalent bond changes (denaturation).

The term "recombinant", as used herein, means that the recombinant vector that can be translated from designed gene into protein fragments and obtained by the gene recombination technology.

The term "bacteria host", as used herein, means the bacterial expression system for exogenous protein production. Many bacterial expression systems are available for the production of foreign proteins. Factors that influence the choice of an expression system include the natural nature of the protein of interest, the experience of the user, and the intended use of the product. *E. coli* is the most commonly used bacterial expression system for expressing foreign proteins.

The term "refolded", as used herein, means the process by which an artificially denatured protein acquires its functional structure and conformation. Through this physical process, the protein is folded from random coils into a specific functional three-dimensional structure. When translated from mRNA sequences into linear peptide chains, proteins initially exist as unfolded polypeptides or random coils, and refolded into native conformation by "natural" or "artificial" means.

The term "inclusion body", as used herein, means the high-density (1.3 mg/ml) insoluble protein particles wrapped by membranes formed when exogenous genes are expressed in prokaryotic cells, especially when they are over-expressed in *E. coli*, which are present as high refraction area and obviously different from other components in the cytoplast when observed under a microscope. Inclusion bodies generally contain more than 50% of recombinant proteins, wherein the rest are ribosomal elements, RNA polymerase, endotoxin, outer membrane proteins, liposomes, lipopolysaccharides, etc., and are only soluble in denaturing agents such as urea, guanidine hydrochloride, etc. The size of inclusion bodies is about 0.5-1 μm, and the diameter of inclusion bodies in *E. coli* cytoplasm is generally between 0.2 μm and 1.5 μm.

The term "wild-type", as used herein, means the native, original proteins from their natural sources, such as human and mouse; or in case of a recombinant protein, the protein is expressed in its original natural sequence without mutation The term "mutant type", as used herein, means using genetic engineering method (such as PCR) to introduce mutations in individual amino acid of a native or "wild-type" proteins.

ABBREVIATIONS

"AMI" represents Acute Myocardial Infarction;
"AD" represents Alzheimer's disease;
"α2-AP" represents α2-antiplasmin;
"AHA" represents American Heart Association;
"Aβ" represents β-amyloid;
"APP" represents β-amyloid precursor protein;
"CDT" represents Catheter-directed thrombolysis;
"IPF" represents idiopathic pulmonary fibrosis;
"μPlm" represents microPlasmin;

"PAD" represents peripheral arterial disease;
"PAO" represents peripheral arterial occlusion;
"Plm" represents plasmin;
"Plg" represents plasminogen;
"PAI" represents plasminogen activator inhibitor;
"tPA" represents tissue-type plasminogen activator;
"uPA" represents urokinase-type plasminogen activator;
"mPlg" represents miniPlg;
"μPlg" represents microPlg;
"mPlm" represents miniPlm;
"μPlm" represents microPlm;
"PA" represents plasminogen activator;
"α2-AP" represents α2-antiplasmin;
"FDP" represents fibrin degradation product;
"rmsd" represents root mean square deviation;
"Kr" represents kringle;
"CTT" represents C-terminal tail;
"PE" represents pulmonary embolism;
"PDB" represents Protein Data Bank;
"MD" represents molecular dynamics;
"SARS-CoV-2" represents respiratory syndrome coronavirus-2;
"COVID-19" represents coronavirus disease 2019;
"PDB" represents Protein Data Bank.

BRIEF DESCRIPTION OF THE DRAWINGS

FIG. 23(1)-FIG. 23(3) show cDNA and amino acid sequence for variants of native plasminogen. In FIG. 23, together form a sequence and show the cDNA sequence of Native Human plg (SEQ ID NO:1) and the amino acid sequence of Native Human plg (SEQ ID NO:2) (NM_000301.2; GI:186972151). The nucleotide sequence numbers are labeled at the left, and protein sequence numbers (starting from Glu-Plg) are labeled at the right as superscripts. The protein sequence of recombinant mPlg is labeled underlined (Ala440-Asn791), and that of the μPlg is labeled underlined and bold (Ala542-Asn791). Among them, cDNA sequence of mPlg in Native Human plg can refer to SEQ ID NO: 3; amino acid sequence of mPlg in Native Human plg can refer to SEQ ID NO: 4 starting from Ala440; cDNA sequence of μPlg in Native Human plg can refer to SEQ ID NO: 5; amino acid sequence of μPlg in Native Human plg can refer to SEQ ID NO: 6 starting from A1a542. FIG. 24 shows nucleotide and amino acid sequence of loops in mutative Human μPlg known in the art, respective sequences can be described as:

Figure 1:
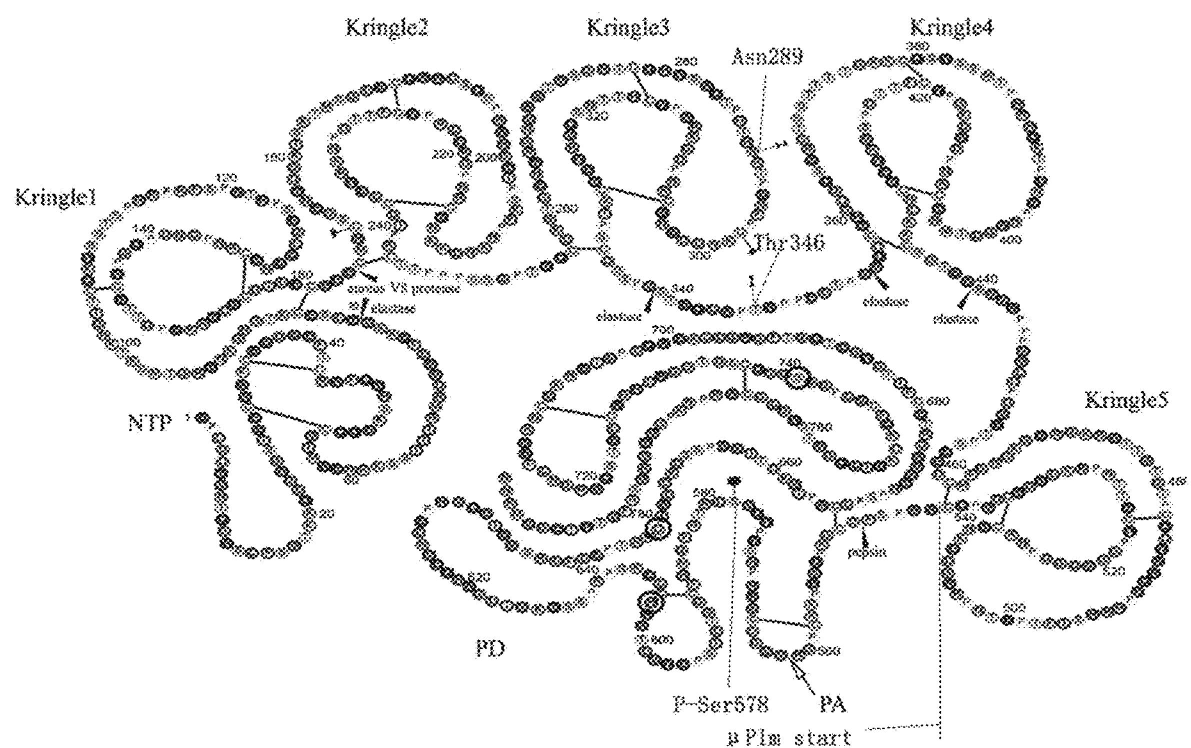
FIG. 1 shows the structure and whole protein sequence of Plg, wherein PD represents protease domain (residues Ala542-Asn791); Kringle1-5 represent kringle domains; NTP represents N-terminal peptide (residues 1-77); ⧗ represents glycosylation sites (Asn289, Thr346); ● represents phosphorylation site (Phe578); big arrow marked as PA indicates the Arg561-Val562 bond cleaved by plasminogen activators; small arrows are cleavage sites by other proteases; ✸ represents cysteine residues forming the S—S bond between K2 and K3; ○ represents active site residues (His603, Asp646, Ser741).

- cDNA sequence of Loop 1 in mutative Human plg can refer to SEQ ID NO: 7, wherein the cDNA starts from g298 to a312; amino acid sequence of Loop 1 in mutative Human μplg can refer to SEQ ID NO: 8, wherein the amino acid starts from Glu1 to Lys5;
- cDNA sequence of Loop 2 in native Human μplg can refer to SEQ ID NO: 9, wherein the cDNA starts from t190 to a213; amino acid sequence of Loop 2 in mutative Human μplg can refer to SEQ ID NO: 10, wherein the amino acid starts from Leu1 to Pro8;
- cDNA sequence of Loop 3 in mutative Human μplg can refer to SEQ ID NO: 11, wherein the cDNA starts from a118 to g132; amino acid sequence of Loop 3 in mutative Human μplg can refer to SEQ ID NO: 12, wherein the amino acid starts from Thr1 to Met5;
- cDNA sequence of Loop 4 in mutative Human plg is cagggtgac; amino acid sequence of Loop 4 in mutative Human μplg is QGD;
- cDNA sequence of Loop 5 in mutative Human μplg can refer to SEQ ID NO: 13, wherein the cDNA starts from t655 to t669; amino acid sequence of Loop 5 in mutative Human μplg can refer to SEQ ID NO: 14, wherein the amino acid starts from Ser1 to Gly5;
- cDNA sequence of Loop 6 in mutative Human μplg can refer to SEQ ID NO: 15, wherein the cDNA starts from a526 to a549; amino acid sequence of Loop 6 in mutative Human μplg can refer to SEQ ID NO: 16, wherein the amino acid starts from Asn1 to Glu8.

DETAILED DESCRIPTION OF THE INVENTION

As set forth, the invention describes a concept and product that in developing Plm-based therapeutics, such as μPlm-based thrombolytic, it is desirable to design a therapeutics to escape or overcome inhibition by α2-AP while being effective in dissolving disease-causing blood clots, but also lost activity after therapeutic actions, because of instability in vivo and short in vivo half-life, avoiding bleeding side effects. The concept and product is "novel" because the conventional view is that in developing protein therapeutics including thrombolytics, more in vivo stability and longer in vivo half-life is always desirable.

Therefore, the first aspect of the present invention provides a short in vivo half-life and in vivo unstable recombinant μPlm including a wild type and a mutant type, which can be just in vivo unstable in a right degree of activity to be long enough to dissolve disease-causing blood clots but not long enough to dissolve the protecting hemostatic plugs, wherein the present disclosure also disclose that some of the mutant types can be characterized to be better or to be almost the same with the wild type. In the serum, the activity of Plm is neutralized by its principle inactivator, α2-AP and has a plasma half-life of only 0.2 seconds. In vivo, α2-AP binds to specific lysine residues located in Kr5 and other Kr domains first and then the catalytic domain. Through protein surface recognition around the active site pocket, α2-AP can also directly bind to μPlm, which has a relatively longer plasma half-life than plasmin—about 4 seconds, which in many cases is still too short for developing an efficient therapeutic drug to cleave and inactivate pathogenic protein or peptide substrates in serum or tissues. Given this, the in vivo half-life of the recombinant μPlm of the present disclosure is designed and chosen to be in the range from about 2.75 to about 28.5 minutes, which is scope long enough to dissolve disease-causing blood clots, but short enough to lost activity after therapeutic actions, thereby avoiding bleeding side effects.

In order to produce such a recombinant μPlm, the inventor of the present disclosure have used a structure-based protein engineering strategy with the goal of increasing the catalytic activity of μPlm and at the same time, resisting α2-AP inhibition. And this strategy provides a new approach of using "directional structure-based protein engineering" for μPlasmin based therapeutic drug development. In addition and more importantly, the novelty of the present invention is the disclosure of a new theory, which is described as: contrary to the conventional approach of developing more stable, longer in vivo half-life protein or enzyme therapeutics, here the inventor of the present disclosure propose a new "hit and die" strategy, in which an "ideal" thrombolytic drug hits the targeting thrombi, dissolving them and die out, avoiding bleeding side effect resulting from the continued activity of present thrombolytic drugs. Therefore, the inventor of the present disclosure proposes to develop unstable, short in vivo half-life thrombolytic therapeutics to reach good drug efficacy and at the same time, avoid bleeding side effect.

I. Primary structure of Plg and its Des-Kringle Derivatives

A brief to primary structure of Plg and its Des-kringle Derivatives is introduced hereby for the following specification of "directional structure-based protein engineering".

Plg (cDNA sequence refers to SEQ ID NO:1 and amino acid sequence refers to SEQ ID NO: 2), whose structure is shown in FIG. 1, is a single-chain glycoprotein, consisting of 791 amino acids, which circulates inertly in the blood, but can bind to fibrin at newly formed blood clots. Biologically, the activation of Plg is enabled by digestion of the peptide bond between Arg561 and Val562 (the site showed by the arrow with PA) by tPA or uPA, both of which directly activate Plg to Plm by cutting the Arg561-Val562 (see FIG. 1) bond. The newly formed Plm then actively digests the fibrin in the clot, thereby dissolving it.

The activated Plg is transformed into 2 separate subunits, but they remain interconnected through 2 disulfide bonds to form the Plm polypeptide, which consists of a longer subunit, called A chain and a shorter component, called the B chain. A chain consists of 5 triple-loop disulfide Kr domains (approximately 78-80 amino acids each). B chain contains a "linker" region of about 20 amino acids and a serine protease domain (approximately 228 amino acids, see FIG. 1).

mPlg (cDNA sequence refers to SEQ ID NO:3 and amino acid sequence refers to SEQ ID NO: 4) and μPlg (cDNA sequence refers to SEQ ID NO:5 and amino acid sequence refers to SEQ ID NO: 6) are 2 des-kringle variants of Plg, wherein mPlg is a mini version of Plg, consisting of only Kr5, the linker and the serine protease domains, whereas μPlg consists of only the linker and serine protease domain itself. Initially, mPlg was produced by digestion with neutrophil elastase shown in FIG. 1 between Ala440 and Ser441 while μPlg was produced by base-mediated cleavage at pH 11 and starts between Cys541 and Ala542. Similar to Plg activation, both mPlg and μPlg can be activated to mPlm and μPlm respectively, by digestion at the peptide bond between Arg561 and Val562 by tPA, uPA or other PAs, again forming 2 separate subunits interconnected by the same 2 disulfide bonds. Removal of either one or both of these disulfide bonds by mutagenesis renders the activated serine protease domain non-functional.

There are some interesting functional differences between Plm, mPlm and μPlm. Functionally, μPlm is distinguished from mPlm and Plm in its inability to specifically bind to fibrin; the fibrin binding resides in Kr1-Kr3 and Kr5 domains, which μPlm lacks. While Plm and mPlm have similar catalytic rates in digesting fibrin, μPlm is 6-fold slower than mPlm and 12-fold slower than Plm. The half-life of plasmin bound to the fibrin surface is estimated to be 2-3 orders of magnitudes longer than freely circulating activated plasmin. Once the fibrin bound Plm dissociates from the blood clot it becomes immediately accessible to its principle inactivator α2-AP and has a plasma half-life of only 0.2 seconds. In vivo, α2-AP binds to specific lysine residues located in Kr5 and other Kr domains first and then the catalytic domain. Through protein surface recognition around the active site pocket (see FIG. 2-6 for structural modeling), α2-AP can also directly bind to μPlm, which has a relatively long plasma activity half-life of about 4 seconds compared to Plm.

Regarding to fibrin specificity, it should be realized that Plm trapped into the clots resulting from Plg activation is different from Plm-based drugs injected into the blood. The trapped Plm, as described above, binds to the inside of the fibrin network and has an activity half-life of 2-3 orders of magnitude than free Plm. In case of drug delivery, a large therapeutic dose of Plm-based drug needs to be delivered to solve an emergency situation, such as ischemic stroke and myocardial infarction and it is unlikely that there is enough time to reach equilibrium to use the fibrin specificity to "target" the disease-causing thrombi and at the same time, to avoid α2-AP inhibition. Practically, currently catheter-directed delivery is the main solution for fibrin targeting. The inventor of the present disclosure speculated that in this artificial emergency situation, fibrin specificity of the thrombolytic drug may not be as important as timing and quantity of delivered therapeutics in terms of drug efficacy. As an example, a comparison is made among local catheter-mediated delivery of serum-derived Plm, recombinant human μPlm isolated from the yeast *P. pastoris* and recombinant tPA in efficacy of dissolution of thrombi in a rabbit extracorporeal loop thrombolysis model. All three molecules were effective at dissolving thrombi in a dose-dependent manner, with similar molar doses for plasmin and μPlm displaying similar efficacy of thrombus dissolution. Plm and μPlm did not result in bleeding at an extra-thrombus hemostatic stable plug far away from the site of infusion at the administered doses. tPA however, did cause bleeding at all concentrations at the extra-thrombus plug site. Thus μPlm, which lacks the kringle domains of Plm and therefore does not possess the extra-fibrin binding specificity, is as effective as Plm at a similar pharmacological dose.

II. Principle of the "Directional Structure-Based Protein Engineering"

Firstly, the specification for the amino acid point mutation of Plg polypeptide is introduced, which establishes the first part of "directional structure-based protein engineering", the principle of which is shown in FIG. 1.

FIG. 1 shows three major post-translational modification sites in human, which influence the in vivo activity, stability and binding affinity to fibrinogen. Clearly shown in the crystal structure of full-length Plg, the O-glycosylation site (Thr346, see FIG. 1) is present in all forms of circulated Plg and protected the zymogen from "accidental" or unwanted activation, while the N-glycosylation site (Asn289, see FIG. 1) is present only in Type I Plg, which favors the more active open conformation. In addition, a phosphorylation site at the Ser578 position has also been identified, which may influence the stability of the molecule. The biological activators of Plg are tPA and uPA, both of which directly activate Plg to Plm by cutting the Arg561-Val562 (see FIG. 1) bond.

Figure 2:
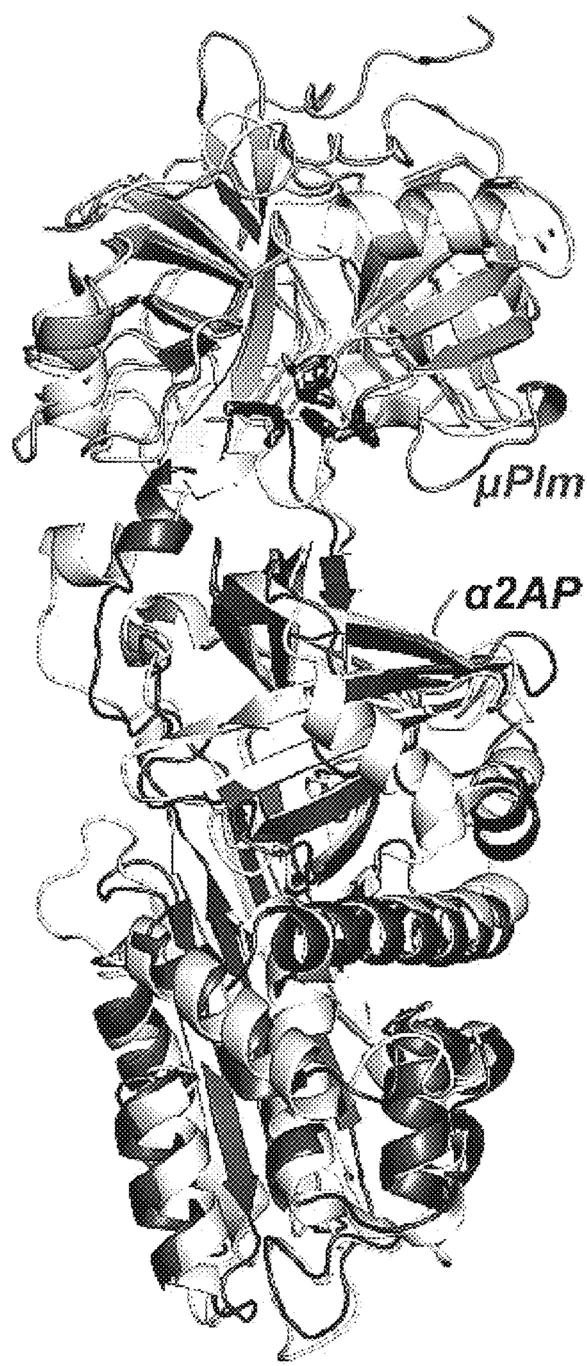
FIG. 2 shows the overall architecture of the μPlm: α2-AP complex, which is modeled by superimposing to the template Trypsin: α1PI (highlighted in white) crystal structure.
Figure 3:
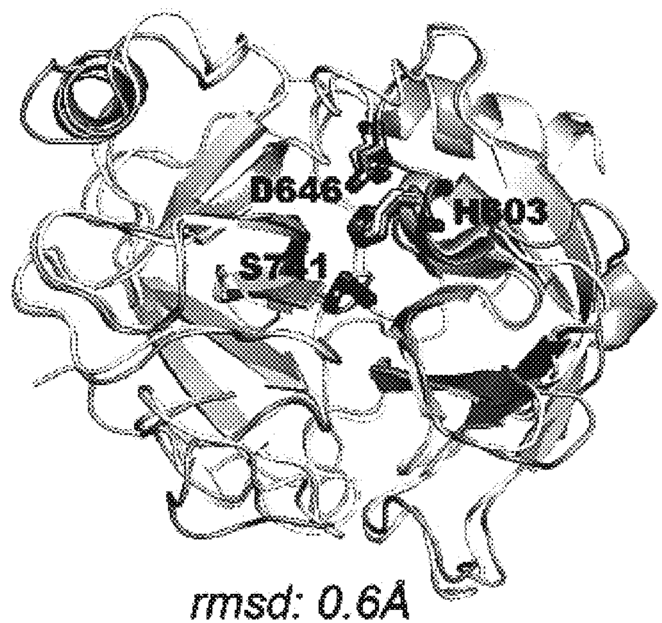
FIG. 3 shows the structural overlay of μPlm and Trypsin with rmsd of 0.6 Å and illustration of the catalytic triad of residues Ser741, His603 and Asp646.
Figure 4:
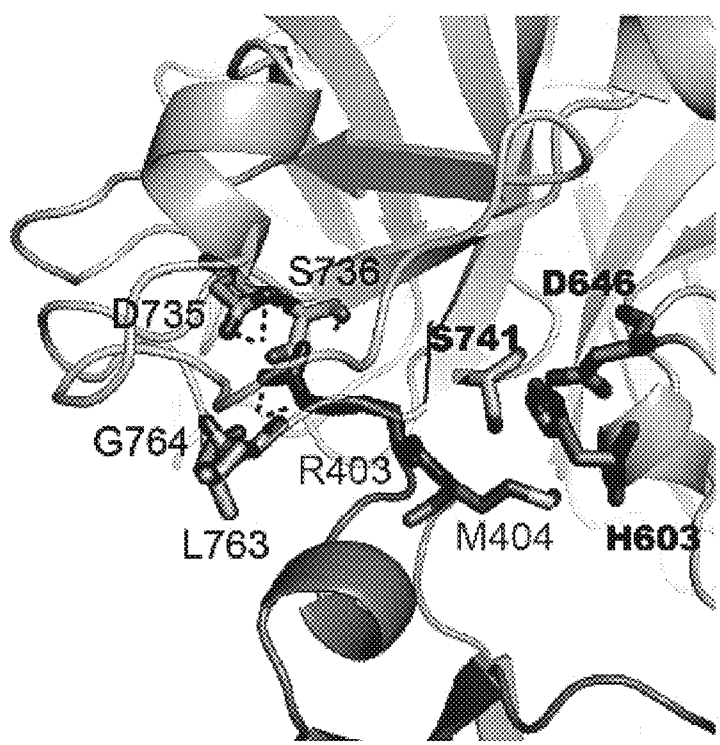
FIG. 4 shows the detailed view of interaction profile in the active site, where the catalytic triad initiates the covalent reaction with the backbone amide between Arg403 and Met404 of α2-AP, wherein the active site is stabilized by extensive hydrogen bonds with the side chain of key residue Arg403.

Secondly, the specification for Homology Modeling and Molecular dynamics Simulation of Plg polypeptide is introduced, which establishes the second part of "directional structure-based protein engineering", the principle of which is shown in FIGS. 2-4.

As shown in FIG. 2, inventors of the present invention constructed a model for the complex structure according to the homologous structure of the trypsin-antitrypsin complex to design mutants capable of escaping inhibition, using the crystal structures of μPlm (PDB code: 1BML) and α2-AP (PDB code: 2R9Y). These two structures are then superimposed to the crystal structure of the Trypsin: antiTrypsin complex (PDB ID: 1OPH).

FIG. 3 shows an expanded view of the overlay of the active site structures of μPlm and trypsin, highlighting the catalytic triad of residues Ser741, His603 and Asp646 of Plm, with backbone rmsd of 0.6 Å. This figure shows a closely fitted central structure of the two serine proteases.

FIG. 4 shows a detailed view of the initial position of the catalytic reaction (the "suicide reaction"), where the active site serine (Ser741) of μPlm assumes a pre-attacking pose to the backbone amide between Arg403 and Met404 of α2-AP.

Figure 5:
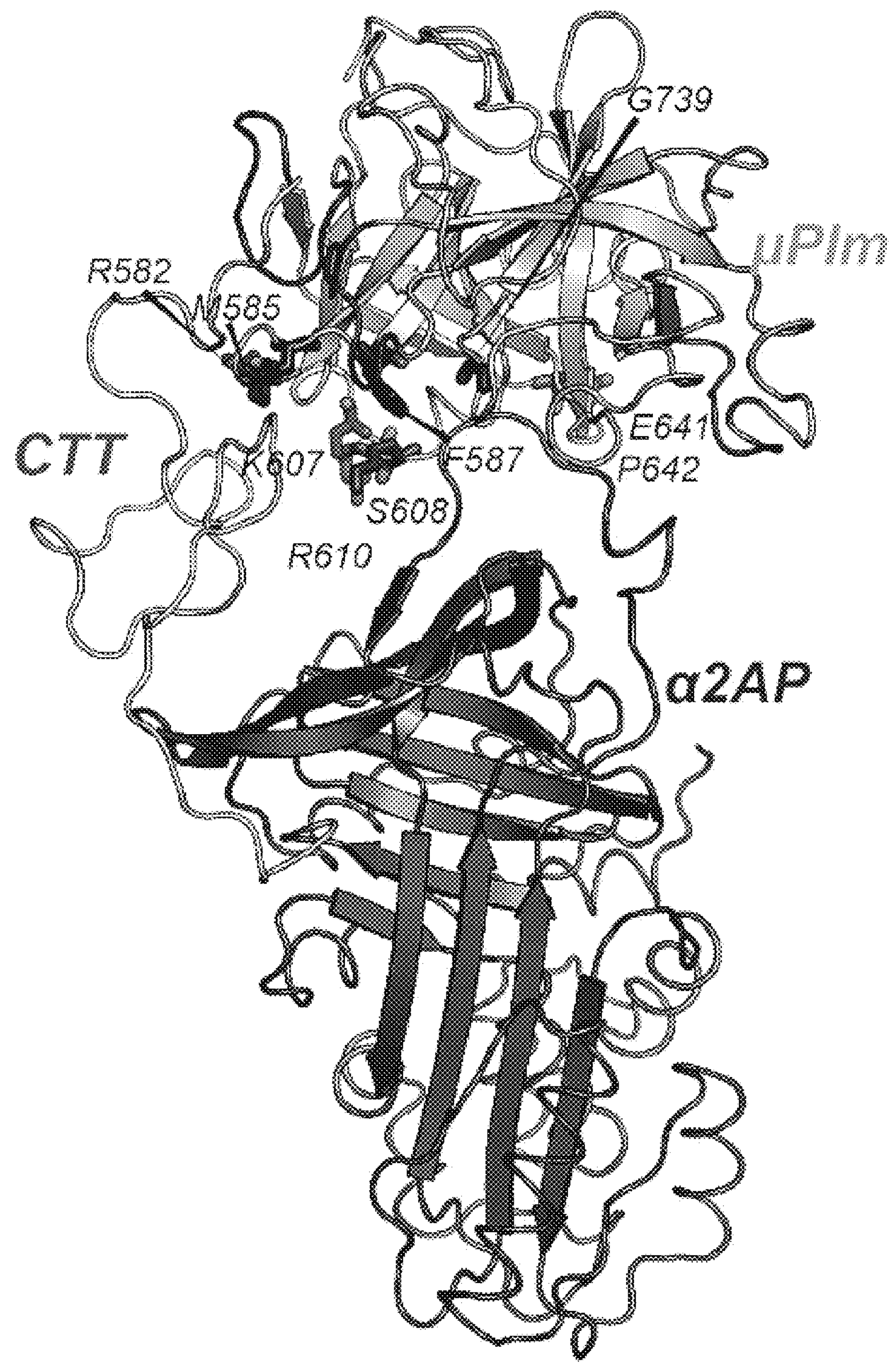
FIG. 5 shows the possible secondary interaction between the disordered C-terminal tail of α2-AP with the autolysis loop and 70-80 loops of Plm, interpreting the mutational effects of these two loops, wherein the key mutations are shown in red stick and labeled accordingly.
Figure 6:
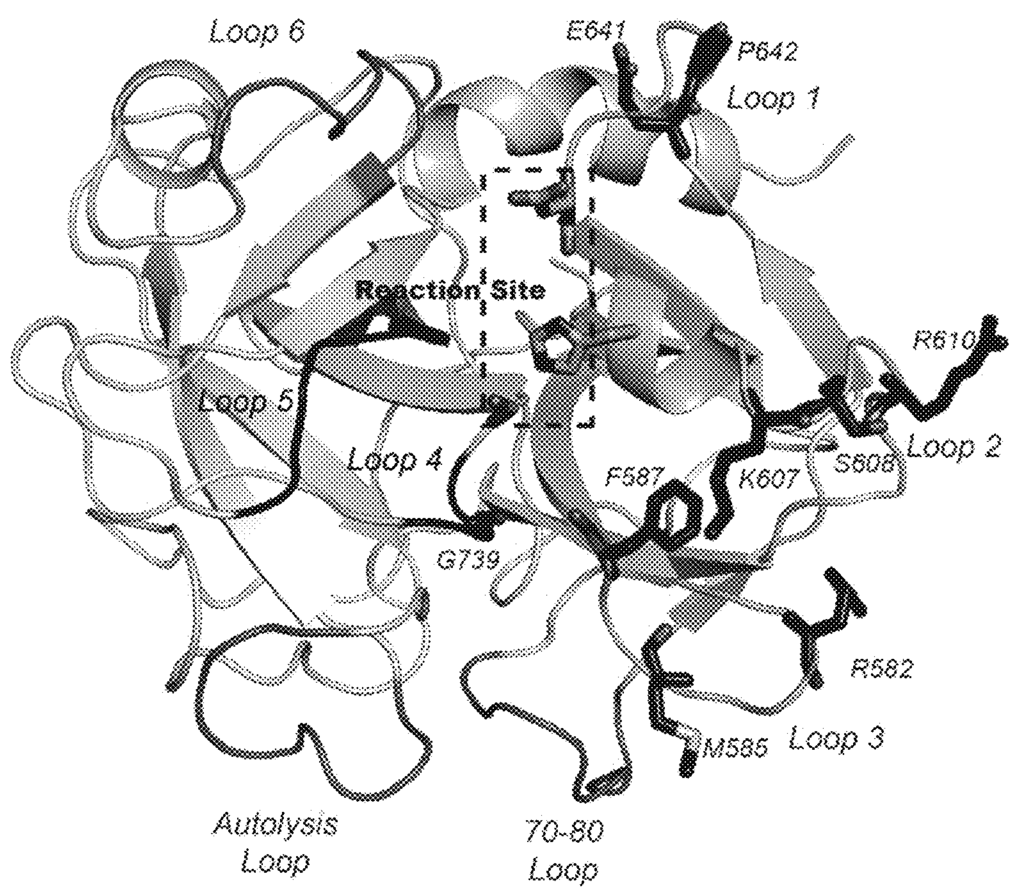
FIG. 6 shows the illustration of the interfacial loops and their mutational effects surrounding the reaction site, where mutations on Loops 1-3 exert moderate perturbation to the active site, with the exception of Phe587. Mutations on Loops 4-5 render the protein inactive, and mutations on other distant loops yield the desired perturbation.

The simulation to the interaction between μPlm and α2-AP is shown in FIGS. 5-6.

FIG. 5 shows the molecular contact regions between μPlm and α2-AP. Because the crystal structure of α2-AP (2R9Y) misses the C-terminal residues, inventors of the p present disclosure used the I-TASSER server to build the missing residues 465-491 (CTT shown in FIG. 6).

FIG. 6 shows 6 loops (cDNA sequence and amino acid sequence thereof refer to SEQ ID NO:7 to SEQ ID NO:16) in the contact surface of μPlm, in addition to the autolysis and 70-80 loops that may have direct contact with the modeled CTT structure.

What discussed in the following is the mechanism by which the bacterial expressed and refolded recombinant μPlm in the present disclosure functions as thrombolytic therapeutics to dissolve disease-causing blood clots but leave the protecting hemostatic plugs intact, thereby avoiding the bleeding side effect, in contract with the mechanism of native Plg and Plm as thrombolytic therapeutics for the treatment of thromboembolism diseases.

Figure 7:
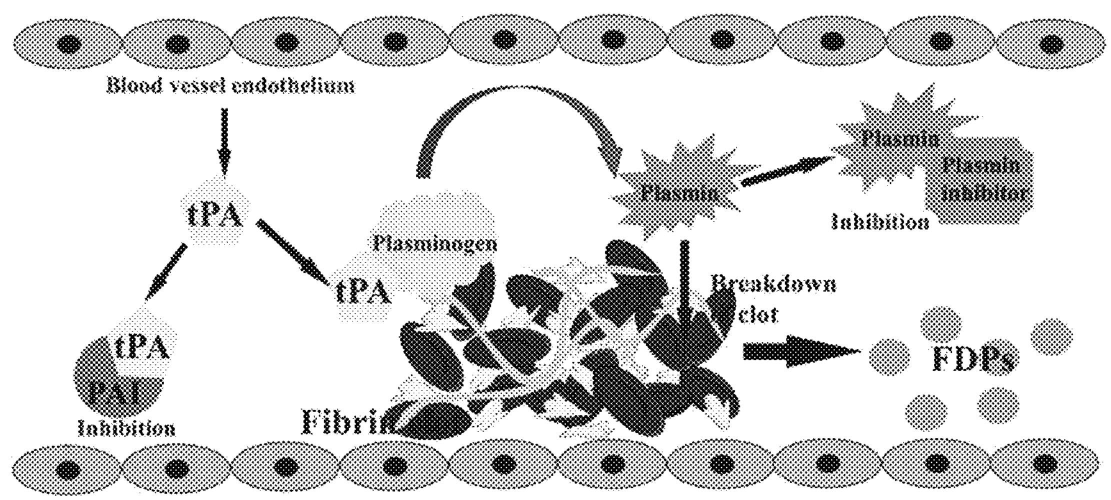
FIG. 7 shows the schematic diagram of Plm digestion of a thrombus.

FIG. 7 shows activation of Plg by tPA in the clot and the degradation of fibrin clot by Plm, which is immediately inactivated by the plasmin inhibitor (α2-AP) when released into the blood. In vivo, the pathogenic thrombi are dissolved into soluble components by the enzyme Plm, a serine protease that is derived from the proenzyme Plg. Plg binds to both fibrin and fibrinogen, thereby incorporating into a clot as it is formed. Both uPA and tPA are exquisitely specific serine proteases which convert Plg to Plm. Other major parts of the blood's intricate fibrinolytic network include the inhibitors such as PAI, which binds to and inhibit tPA and uPA and α2-AP, which binds to and inhibit Plm. A critical physiological function of Plm is shown in congenital Plm deficiency, which causes a multisystemic disorder leading to deficient extravascular fibrinolysis. As a clinical consequence, the wound healing capacity of mucous membranes is markedly impaired, leading to ligneous conjunctivitis and several other manifestations.

First, the PAs do not dissolve blood clots themselves, but it generates active Plm from Plg to do so. While this can be effective in the dissolution of a thrombus in a small myocardial artery, difficulties arise in the dissolution of much larger thrombi in peripheral arteries and veins because the clots are long and retracted. Circulation is poor near these clots so the supply of Plg substrate is insufficient. Consequently, systemically delivered PAs will not only have difficulty infiltrating the clot, but also there is insufficient Plg substrate to enable efficient dissolution of the clot. On the other hand, a Plm-based direct thrombolytic agent can efficiently dissolve the clot by itself, avoiding the Plg substrate depletion problems that are encountered in the treatment of using PAs. Furthermore, once diffused into the serum, Plm activity will be immediately neutralized by α2-AP, potentially avoiding bleeding side effects in case of the active Plm concentration is lower than α2-AP in the serum.

Figure 8:
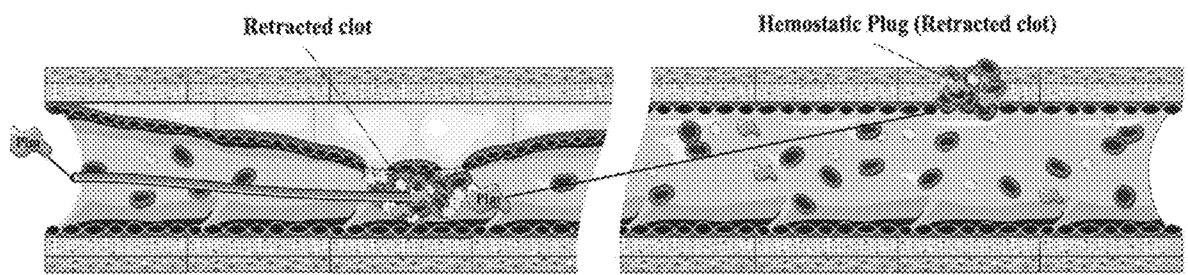
FIG. 8 shows the schematic presentation of two possible actions of Plm and Plm when applied to a local blood clotting, wherein in native Plm therapeutics, after dissolving the retracted blood clots such as in the case of Peripheral Arterial Occlusion, the diffused Plm can still actively dissolve distant retracted haemostatic plugs if the applied Plm can neutralize α2-AP and has longer in vivo half-life, resulting in bleeding side effect.

FIG. 8 shows that the "overdosed" Plm may reach distant hemostatic plugs and dissolving them, causing systemic bleeding. On the other hand, the in vivo "fragile" mutant Plm may be able to dissolve the immediately accessible clots, if enough active materials are delivered and then die out or lost activity quickly after diffusing into the blood, avoiding bleeding side effect. Again, the inventor of the present disclosure like to stress that the definition of the in vivo half-life here is the structural integrity of the enzyme in the blood, as already explained in the Introduction section.

Figure 9:
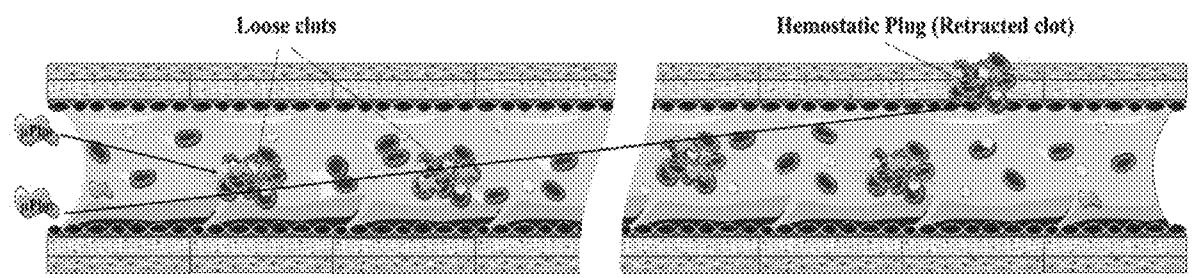
FIG. 9 shows schematic presentation of two possible actions of μPlm and Plm when applied to a systemic blood clotting, wherein in acute systemic clotting, the newly formed clots are un-contracted (un-retracted) or "loose", but the haemostatic plugs formed to protect the blood wall from bleeding are usually contracted (retracted) and "denser". After neutralizing α2-AP in the serum, excessively applied mutant μPlm may quickly dissolve the loose clots in the serum but may not be able to dissolve the retracted haemostatic plugs because of the short in vivo half-life. It is well-known that "loose clots" are much easier to be dissolved than dense, contracted clots. In this figure, represents μPlm/Plm; represents RBC; represents Platelet; represents Fibrin.

FIG. 9 shows that the concentration of delivered μPlm is "overdosed" to neutralize all of the protease inhibitors and "transient" because of the very short in vivo half-life. As shown in FIG. 9, the inventor of the present disclosure propose a possible "hit and die" strategy, which is to engineering a short in vivo half-life version of thrombolytics (such as a *E. coli* expressed mutant μPlm) in such a way that after dissolving the newly formed "loose" clots in acute systemic bleeding, the mutant Plm may die out or lost activity quickly and unable to dissolve the contracted or "dense" hemostatic plugs, avoiding bleeding side effect resulting from the continued activity of the present thrombolytic drugs.

The second aspect of the present invention provides a pharmaceutical composition comprising the above recombinant microplasmin as a thrombolytic agent or a pharmaceutically acceptable dosage form thereof or a pharmaceutically acceptable solvate of said compound or dosage form and including a pharmaceutically acceptable excipient.

Typically, the recombinant microplasmin according to the present disclosure is incorporated into pharmaceutical compositions suitable for administration to a subject, wherein the pharmaceutical composition comprises the recombinant microplasmin and a pharmaceutically acceptable excipient. As used herein, "pharmaceutically acceptable excipient" includes any and all solvents, dispersion media, coatings, antibacterial and antifungal agents, isotonic and absorption delaying agents and the like that are physiologically compatible. Examples of pharmaceutically acceptable excipients include one or more of water, saline, phosphate buffered saline, dextrose, glycerol, ethanol and the like, as well as combinations thereof.

In many cases, it is preferable to include isotonic agents, for example, sugars, polyalcohols such as mannitol, sorbitol or sodium chloride in the composition. Pharmaceutically acceptable excipients may further comprise minor amounts of auxiliary substances such as wetting or emulsifying agents, preservatives or buffers, which enhance the shelf life or effectiveness of the pharmaceutical composition.

The compositions of present disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for intravenous injection or catheter-directed intravenous applications.

Pharmaceutical compositions typically must be sterile and stable under the conditions of manufacture and storage. The composition can be formulated as a solution, microemulsion, dispersion, lyophilized powder or other ordered structure suitable to high drug concentration. Sterile injectable solutions can be prepared by incorporating the active compound (i.e., the pharmaceutical composition) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

III. Dose and Administration

For in vivo applications, recombinant microplasmin are provided or administered in an effective dosage. The phrases "effective dosage" or "effective amount" as used herein refer to an amount of a drug, compound or pharmaceutical composition necessary to achieve any one or more beneficial or desired therapeutic results either directly or indirectly. For example, when administered to a pulmonary embolism subject, an effective dosage includes an amount sufficient to dissolving disease-causing blood clots. A "therapeutically effective amount" of a pharmaceutical composition of the invention refers to an amount effective, at dosages and for periods of time necessary, to achieve the desired therapeutic result. Such therapeutically effective amount may vary according to factors such as the disease state, age, sex and weight of the individual and the ability of the pharmaceutical composition to elicit a desired response in the individual. A therapeutically effective amount is also one in which any toxic or detrimental effects of the pharmaceutical composition are outweighed by the therapeutically beneficial effects.

An effective dosage can be administered in one or more administrations. An effective dosage of a drug, compound or pharmaceutical composition may or may not be achieved in conjunction with another drug, compound or pharmaceutical composition. Thus, an effective dosage may be considered in the context of administering one or more therapeutic agents and a single agent may be considered to be given in an effective amount if, in conjunction with one or more other agents, a desirable result may be or is achieved.

The recombinant microplasmin can be administered to an individual via any suitable route. It should be understood by persons skilled in the art that the examples described herein are not intended to be limiting but to be illustrative of the techniques available. Accordingly, in some aspects of the invention, the recombinant microplasmin is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal oral, inhalation or topical routes. Administration can be systemic, e.g., intravenous administration or localized, e.g., catheter-directed application into the blocking thrombi. Commercially available nebulizers for liquid formulations, including jet nebulizers and ultrasonic nebulizers are useful for administration. Liquid formulations can be directly nebulized and lyophilized powder can be nebulized after reconstitution. Alternatively, the recombinant microplasmin can be aerosolized using a fluorocarbon formulation and a metered dose inhaler or inhaled as a lyophilized and milled powder. The preferred mode of administration is intravenous, subcutaneous, submuscular and aerosol routes. In a preferred embodiment, the pharmaceutical composition is administered by intravenous infusion or injection. In another preferred embodiment, the pharmaceutical composition is administered by catheter-directed application to directly dissolving the blocking thrombi.

In some aspects of the invention, the recombinant microplasmin is administered via site-specific or targeted local delivery techniques. Examples of site-specific or targeted local delivery techniques include various implantable depot sources of recombinant microplasmin or local delivery catheters, such as infusion catheters, indwelling catheters or needle catheters, synthetic grafts, adventitial wraps, shunts and stents or other implantable devices, site specific carriers, direct injection or direct application.

For the purpose of the present invention, the appropriate dosage of the recombinant microplasmin will depend on the particular ADC (antibody-drug conjugate) (or compositions thereof) employed, the type and severity of symptoms to be treated, whether the agent is administered for therapeutic purposes, previous therapy, the patient's clinical history and response to the agent, the patient's clearance rate for the administered agent and the discretion of the attending physician. The clinician may administer a recombinant microplasmin until a dosage is reached that achieves the desired result and beyond. Dose and/or frequency can vary over course of treatment, but may stay constant as well. Empirical considerations, such as the half-life, generally will contribute to the determination of the dosage. For example, the recombinant microplasmin can be effective in dissolving disease-causing blood clots but leaving the protecting hemostatic plugs intact, avoiding the bleeding side effect. Frequency of administration may be determined and adjusted over the course of therapy and is generally, but not necessarily, based on treatment and/or suppression and/or amelioration of symptoms, e.g., tumor growth inhibition or delay, etc. Alternatively, sustained continuous release formulations of recombinant microplasmin may be appropriate. Various formulations and devices for achieving sustained release are known in the art.

For the purpose of the present invention, a typical daily dosage might range from about any of 3 μg/kg to 30 μg/kg to 300 μg/kg to 3 mg/kg, to 30 mg/kg, to 100 mg/kg or more. For example, dosage of about 1 mg/kg, about 2.5 mg/kg, about 5 mg/kg, about 10 mg/kg and about 25 mg/kg may be used. For repeated administrations over several days or longer, depending on the thromboembolism, the treatment is sustained until a desired suppression of symptoms occurs or until sufficient therapeutic levels are achieved, for example, to dissolve disease-causing blood clots. An exemplary dosing regimen includes administering an initial dose of about 2 mg/kg, followed by a weekly maintenance dose of about 1 mg/kg of the recombinant microplasmin or followed by a maintenance dose of about 1 mg/kg every other week. Other exemplary dosing regimens include administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects of the invention, dosing from one to four times a week is contemplated. In other aspects, dosing once a month or once every other month or every three months is contemplated, as well as weekly, bi-weekly and every three weeks. The progress of this therapy may be easily monitored by conventional techniques and assays.

The disclosed pharmaceutical composition may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent or the sum of the therapeutic effects elicited by the single agents of a given combination or at least about five-fold greater or at least about ten-fold greater or at least about twenty-fold greater or at least about fifty-fold greater or at least about one hundred-fold greater. A synergistic therapeutic effect may also be observed as an increase in therapeutic effect of at least 10% compared to the therapeutic effect elicited by a single agent or the sum of the therapeutic effects elicited by the single agents of a given combination or at least 20% or at least 30% or at least 40% or at least 50% or at least 60% or at least 70% or at least 80% or at least 90% or at least 100% or more. A synergistic effect is also an effect that permits reduced dosing of therapeutic agents when they are used in combination.

In certain embodiments, a therapeutically or prophylactically-effective amount of the pharmaceutical composition in the present disclosure is about 0.0001 to 50 mg/kg, about 0.001 to 50 mg/kg, about 0.001 to 5 mg/kg, about 0.001 to 0.5 mg/kg, about 0.001 to 0.05 mg/kg, about 0.01 to 5 mg/kg or about 0.01 to 0.5 mg/kg. In other embodiments, a therapeutically or prophylactically-effective blood or plasma concentration of the pharmaceutical composition in the present disclosure is about 0.0003 to 300 nM, about 0.003 to 300 nM, about 0.03 to 300 nM, about 0.003 to 30 nM, about 0.03 to 30 nM or about 0.3 to 3 nM. Other doses or blood or plasma concentrations are also possible. The concentration of the pharmaceutical composition, for example in blood or plasma, may be measured by any method known in the art.

The pharmaceutical composition may be administered, for example in a composition comprising such variant, once or multiple times to a subject until an adequate therapeutic or prophylactic effect is achieved. Where multiple administrations are used they may administered hourly, daily or at any other appropriate interval, including for example multiple daily doses. Multiple doses may be administered on a schedule such as every 10 minutes, every 15 minutes, every 20 minutes, every 30 minutes, every hour, every 2 hours, every 3 hours, every 4 hours, every 5 hours, every 6 hours, 3 times daily, twice daily, once daily, once every 2 days, once every 3 days, once weekly or on some other schedule. The pharmaceutical composition may also be administered continuously. The pharmaceutical composition may be administered, for example, via a parenteral route (e.g., intravenously, subcutaneously, intraperitoneally or intramuscularly). The pharmaceutical composition will generally be administered as part of a pharmaceutical composition as described herein.

The third aspect of the present disclosure provides a method of treating thromboembolism related diseases including ischemic stroke, myocardial infarction, deep vein thrombosis, peripheral arterial occlusion, pulmonary embolism and systemic blood clotting caused by various disease conditions such as SARS-CoV2 infection and sepsis, wherein the method includes the administration to a subject suffering therefrom a therapeutically effective amount of the above pharmaceutical composition or a pharmaceutically acceptable dosage form thereof or a pharmaceutically acceptable solvate of said compound or dosage form.

VI. Treatment of Cardiovascular Diseases

One of the applications of Plg and Plm based therapeutics is for peripheral arterial occlusion, either alone or in combination with PAs. PAO occurs when a clot blocks artery blood flow to a distant part of the body such as the legs, arms, feet or hands. A classical early hallmark of PAO is “intermittent claudication” or leg pain during the sustained activity which subsides after rest. Continued restriction of blood flow ultimately leads to constant pains in the leg or limb even at rest, along with ulcers, tissue death and gangrene. Ultimately it could result in limb amputation. PAO is the result of PAD, in which atherosclerotic plaque build-up on the artery walls leads to obstructed blood flow, leading to ischemia in blood starved limbs of the body.

Treatment of AMI is fundamentally different from PAO. First, the PAs do not dissolve blood clots themselves, but it generates active Plm from Plg to do so. While this can be effective in the dissolution of a thrombus in a small myocardial artery, difficulties arise in the dissolution of much larger thrombi in peripheral arteries and veins because the clots are long and retracted. Circulation is poor near these clots so the supply of Plg substrate is insufficient. Consequently, systemically delivered PAs will not only have difficulty infiltrating the clot, but also there is insufficient Plg substrate to enable efficient dissolution of the clot. On the other hand, a Plm-based direct thrombolytic agent can efficiently dissolve the clot by itself, avoiding the Plg substrate depletion problems that are encountered in the treatment of using PAs. Furthermore, the short in vivo half-life version of the microplasmin disclosed in this invention will lost activity after dissolving the clot, avoiding bleeding side effects.

V. Treatment of Alzheimer’s Disease

Alzheimer’s Disease is mainly characterized by extracellular plaques and intracellular neurofibrillary tangles. The extracellular plaques are primarily composed of Aβ peptides and the intracellular neurofibrillary tangles are composed of the cytoskeletal protein tau. Aβ is a mixture of the peptide from 38 to 43 residues, which is generated from APP by the action of two proteases, β-secretase (BACE-1) and γ-secretase. Results from the past research have supported the amyloid cascade hypothesis. This hypothesis proposes that the overproduction of Aβ peptides (mostly from genetic defect) or the failure to effectively clear this peptide (most of the sporadic AD cases), leads to AD through Aβ toxicity and amyloid deposition, which is also thought to be involved in the formation of neurofibrillary tangles. As a result, therapeutic research toward the treatment of AD has mainly aimed at blocking production, hindering aggregation or enhancing the clearance of Aβ peptides. One of the earliest AP-based therapeutic applications was immunotherapy using Aβ peptide as a vaccine, although clinical toxicity has prevented further development of this strategy. Using antibodies to Aβ peptides as therapeutic agents have also been conducted in many clinical trials.

In normal physiological conditions, the production of Aβ is counterbalanced by its elimination via multiple interrelated processes acting in concert, including proteolytic degradation, cell-mediated clearance, active and passive transport out of the brain, as well as deposition into insoluble aggregates. Although each of these processes contributes to Aβ catabolism, research results emerged have shown that proteolytic degradation is a particularly important regulator of cerebral Aβ levels and, by extension, AD pathogenesis. Saido and colleagues were the first to examine Aβ degradation in the living animal. Subsequent works have identified many different kinds of proteolytic enzymes involved in Aβ catabolism, including zinc-metalloproteases, cysteine proteases and serine proteases. All of these enzymes have potential therapeutic value for treating AD. However, of all the proteases that are directly involved in degrading Aβ in vivo, only Plm has been extensively studied as a therapeutic drug. Therefore, presently, developing Plm-based therapeutics is a practical choice among the Aβ degradation enzymes.

Studies in cultured cells have shown that purified Plm significantly decreases the level of neuronal injuries induced by aggregated Aβ. In separate research, Ledesma et al have not only shown that Plm degrades Aβ, converting it from the amyloidogenic form to a non-amyloidogenic form, but have also shown consistently that the level of Plm is reduced in brain tissues from AD patients. Published results have also shown that peripherally applied Aβ-containing inoculate induced cerebral β-amyloidosis, further implying that clearing peripheral Aβ can be as important as cerebral clearance.

As described above, native plasmin-based therapeutics may not be efficient enough for therapeutic application. However, a Plm-based escaping mutant may be selected such that it can specifically cleave and detoxify the β-Amyloid peptide, but at the same time, have low catalytic activities toward other common substrates such as fibrin, in addition to resisting α2-AP inhibition. The tailor-selected mutant Pm-based therapeutics may therefore have higher efficacy toward treating AD but with reduced side effects.

VI. Treatment of Pulmonary Fibrosis

Reduced fibrinolysis due to Plm downregulation has been implicated in lung fibrosis. It has been shown that mice with targeted deletion of the Plg gene have poor outcomes in pulmonary fibrosis conditions. It has also been shown that mice with overexpression of a PAI-1 developed impaired systemic Plg activation to Plm, resulting in a more severe lung fibrotic response following bleomycin injury than do littermate controls and increased Plg activation has anti-fibrotic effects. On the other hand, the Plg activation system is impaired in IPF, further proving that the Plg activation system is critical for preventing the IPF disease.

VII. Treatment of COVID-19 Caused Systematic Thrombosis

The coagulopathy of COVID-19 patients usually shows increased fibrin degradation products (D-dimers) and fibrinogen levels, but the platelet count and prothrombin time are initially normal. The high incidence of venous thromboembolism and the importance of treating with anti-coagulant thromboprophylaxis have been stated in a guidance document for treating COVID-19. Anticoagulant treatment with heparin has shown an improved prognosis for patients admitted to intensive care units. High levels of D-dimers and prolonged prothrombin time were also observed in ICU patients in another report.

In the advanced clinical stages of highly pathogenic human coronavirus (hCoV), comorbidities are important factors in the occurrence of disease complications that often lead to death. The most common comorbidities of severe COVID-19 patients are reported to be diabetes, hypertension, malignancies, kidney dysfunction and chronic obstructive pulmonary disease (COPD), all of which are characterized by chronic inflammation. Blood flow abnormalities, endothelial dysfunction, hyperviscosity and platelet activation caused by hypoxia, hypercoagulability and immune reactions are the main factors that lead to thrombogenesis and high doses of heparin therapy are usually applied in the treatment of COVID-19-induced thrombosis.

A common feature in patients with underlying diseases is elevated blood Plg levels. Studies aimed at exploring new approaches both for early detection and for the treatment of severe COVID-19 patients can have a major impact on the fight against the disease. Herein, the inventor of the present disclosure highlight evidences that support the potential role of the Plasminogen Activator/Plasminogen Activator Receptor (PA/PAR) system in the pathogenesis of COVID-19 associated pneumonia and acute respiratory distress syndrome (ARDS). A soluble form of uPAR could be a potential biomarker for the progression of the disease and its level correlates with comorbidities associated with the death of COVID-19 patients. In a study involving 118 hospitalized COVID-19 patients, elevated levels of tPA and PAI-1 were found in COVID-19 patients and were associated with more severe respiratory conditions.

Targeting the dysregulated PA/PAR system may represent a therapeutic approach for the treatment of severe lung injury caused by SARS-CoV-2 infections. Several studies in animal models as well as a phase I clinical trial support the use of PA to limit Acute Respiratory Distress Syndrome (ARDS) progression and reduce ARDS-induced death. COVID-19 induced ARDS could be caused by the presence of microthrombi, which could be treated with thrombolytic enzyme therapeutics. In a study of 13 COVID-19 patients, Plg inhalation treatment has been reported, showing improvement in lung lesions and hypoxemia. Three more case series with a total of eight cases of ARDS caused by COVID-19 are found benefitted from tPA administration. There are evidence clearly indicates a positive therapeutic effect for treating COVID-19 related systemic blood clotting with thrombolytic agents. The Plm-based thrombolytic therapeutics described in the following sections may provide alternative or better therapeutic options than PA-based therapeutics. For comparison, a SARS coronavirus infection leads to lung fibrosis in late-stages of severe patients. Not surprisingly, IPF is a major risk factor for COVID-19, which in many cases can lead to long-term pulmonary fibrosis. The resulting lung fibrosis is related or may be a result of virus-induced coagulation, because it has been implied that SARS-CoV-2 caused lung injury can lead to extravascular coagulation in the interstitial space and lung fibrosis. The fibrosis, at least in the initial stage, could be treated with Plm-based direct thrombolytic therapeutics. In fact, it has been shown in both animal model and initial clinical trials, that Plg supplementation can be a promising therapeutics for IPF treatment.

EXAMPLES

The following examples are offered for illustrative purposes only and are not intended to limit the scope of the present invention in any way. Indeed, various modifications of the invention in addition to those shown and described herein will become apparent to those skilled in the art from the foregoing description and fall within the scope of the appended claims.

In a previous publication, the inventor of the present disclosure described the screening and characterization of a total of 71 μPlm mutant clones, in order to select μPlm variants the can escape α2-AP inhibition and also have good enzyme activity. Based on the previous results, in this study, the inventor of the present disclosure focused on *E. coli* expression, inclusion body refolding and purification of three recombinant μPlgs, which include wild-type human μPlg (H-μPlg), wild-type mouse μPlg (M-μPlg) and a selected α2-AP escape mutant of H-μPlg, PHE587ALA (H-PHE587ALA). In addition, in order to compare the biochemistry and kinetic properties of *E. coli* and yeast expressed Plg and Plm, the inventor of the present disclosure cloned both of the H-μPlg and M-μPlg into a yeast expression vector and expressed and purified the yeast expressed recombinant proteins (HY-μPlg and MY-μPlg).

Example I. Cloning, Expression, Inclusion Body Refolding and Purification of μPlm A synthetic gene of human and mouse μPlg optimized for *E. coli* expression was cloned into a pET-11 expression vector for *E. coli* expression. The sequence verified wild-type and mutant plasmids were transformed into *E. coli* strain BL21(DE3) for expression, refolding and purification following the same procedure as previously described (Dan M, Tuan M, Liu W; Wu S, Lin X (2007) *Refolding, purification and activation of mPlm and μPlm isolated from E. coli inclusion bodies. Protein Expression & Purification* 52, 0-402). Briefly, *E. coli* containing the expression plasmids was expressed in a high-density shaker flask auto-induction system (Studier F W (2005) Protein production by auto-induction in high-density shaking cultures. Protein Expression and Purification 41, 207-234). The broth was then spun down and the pellet was washed extensively and put through freeze thaw cycles with lysozyme to purify the inclusion bodies. The purified inclusion bodies were dissolved in an 8 M urea buffer (8 M urea, 0.1 M Tris, 1 mM glycine, 1 mM EDTA, 10 mM b-mercaptoethanol, 10 mM dithiothreitol (DTT), 1 mM reduced glutathione (GSH), 0.1 mM oxidized glutathione (GSSG), pH 10.5 with a final concentration of 2 mg/ml). The solution was rapidly diluted into 20 volumes of 20 mM Tris, 0.2 M L-arginine, pH 10.5. The pH of the solution was slowly adjusted to pH 8 with 6 M HCl as described (Lin X, Umetsu T (2010) *by using the High pH and pH-Shift Refolding Technology. Current Pharmaceutical Biotechnology* 11, 293-299). The refolded protein was then concentrated by ultrafiltration and purified by various types of column chromatography as described (Dan M, Tuan M, Liu W; Wu S, Lin X (2007) *Refolding, purification and activation of mPlm and μPlm isolated from E. coli inclusion bodies. Protein Expression & Purification* 52, 0-402).

The *E. coli* expressed insoluble recombinant microplasmin is refolded and purified into an active form for thrombolytic applications.

To experimentally map the contribution of individual residues to the complex formation, the inventor of the present disclosure changed each of the amino acid residues in the μPlm loops into alanine (by means of alanine scanning mutagenesis) and made 54 alanine mutations and 52 of them were expressed in *E. coli* as inclusion bodies, refolded and purified. From kinetic data of the mutant proteins, the inventor of the present disclosure identified Phe587Ala as the most desirable mutant and performed saturation mutagenesis on the Phe587 position. Interestingly, the α2-AP resistant Phe587Ala mutant is consistent with published results showing that the same mutant is resistant to certain active-site small molecule inhibitors. Together the inventor of the present disclosure made a total of 73 mutant clones, 71 of these can be expressed and purified. Table 1 listed the kinetic parameters of the 9 most promising mutants selected from our mutagenesis results. The table summarized the best mutants obtained from the alanine scanning mutagenesis data from reference. All of the kinetic values of the mutants are expressed as relative to the μPlm wild-type enzyme (WT, set to be 1), which has Kcat=442 ($min^{-1}$) and Km=204 μM. Kcat/Km is the catalytic efficiency and IC50 is the inhibition of μPlm by α2-AP to half of the maximum activity. In the last column, Kcat/Km×LC50 represents an artificial value to define an "escaping efficiency index". ∞ means no inhibition.

TABLE 1

Summary of key desired mutants.

| Loops | Mutants | Kcat | Km | Kcat/Km | IC50 | Kcat/KmIC50 |
|---|---|---|---|---|---|---|
| | WT | 1.0 | 1.0 | 1.0 | 1.0 | 1.0 |
| 1 | Glu641Ala | 0.7 | 0.6 | 1.1 | 1.6 | 1.8 |
| | Pro642Ala | 1.6 | 0.7 | 2.2 | 1.0 | 2.2 |
| 2 | Lys607Ala | 2.9 | 0.9 | 3.3 | 1.0 | 3.3 |
| | Ser608Ala | 2.2 | 1.2 | 1.9 | 1.2 | 2.3 |
| | Arg610Ala | 1.6 | 1.0 | 1.6 | 1.7 | 2.7 |
| 3 | Arg582Ala | 2.0 | 1.0 | 2.0 | 1.6 | 3.2 |
| | Met585Ala | 2.3 | 0.8 | 3.1 | 1.2 | 3.7 |
| | Phe587Ala | 2.6 | 0.9 | 2.9 | 3.9 | 11.3 |
| 4 | Gly739Ala | 0.6 | 4.9 | 0.1 | ∞ | ∞ |

In the table, a column termed Kcat/Km×IC50 is listed, which the inventor of the present disclosure defined as a mutant "escaping efficiency index"—the higher the index number, the better the mutant. The index number for Phe587Ala is 11.3, higher than any other mutants, except Gly739Ala, which is out of scale and requires more detailed studies. Each of the mutant residues is labeled in the structures of FIG. 3, which showed that 3 mutants are in contact with the modeled CTT structure (Arg582Ala, Met585Ala, Lys607Ala) and 5 are in contact with the reactive center loop structure of α2-AP (Lys607Ala, Ser608Ala, Arg610Ala, Glu641Ala, Pro642Ala). Phe587Ala is the most promising escape mutant selected, with catalytic activity and efficiency better than the WT but highly resistant to α2-AP inhibition. The Gly739 position is very close to the active site Ser741 and Gly739Ala has lower catalytic efficiency toward the synthetic substrate, but kinetic data show that this mutant is completely avoided of inhibition by α2-AP. These results opened new doors for further research toward the therapeutic development of Plm-based drugs. The ultimate goal is to find engineered μPlm therapeutics that will be specific toward degrading a targeted pathogenic peptide substrate, but has no or much lower activity toward other untargeted substrates, through structure-based "directional engineering" of the enzyme.

Figure 11:
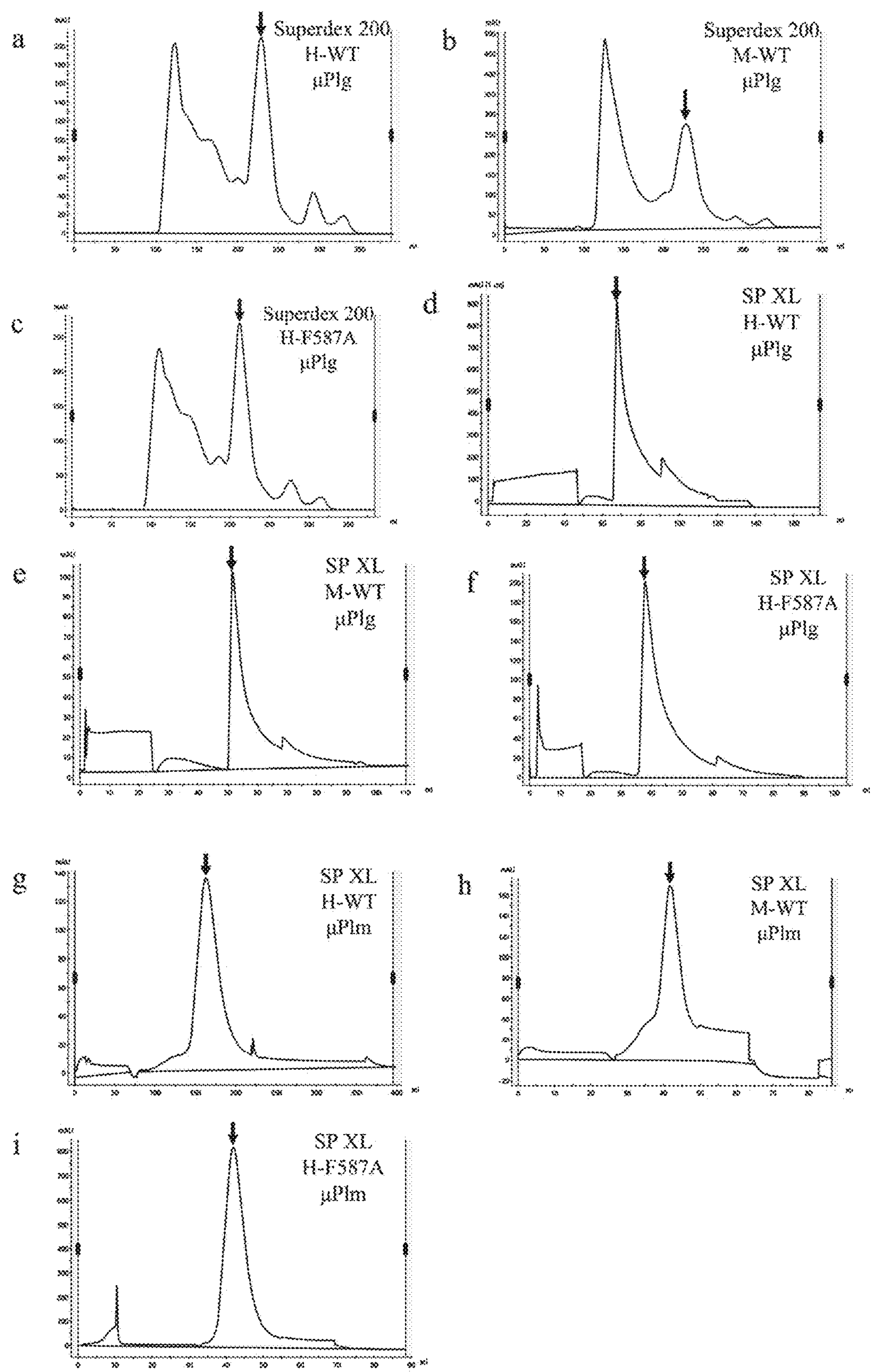
FIG. 11 shows μPlg and μPlm purification by Superdex 200 SEC and SP XL cation exchange column chromatography. (a) H-WT μPlg purification by Superdex 200; (b) M-WT μPlg purification by superdex 200; (c) H-Phe587Ala μPlg purification by Superdex 200; (d) H-WT μPlg purification by SP XL; (e) M-WT μPlg purification by SP XL; (f) H-Phe587Ala μPlg purification by SP XL; (g) H-WT μPlm purification by SP XL; (h) M-WT μPlm purification by SP XL; (i) H-Phe587Ala μPlm purification by SP XL, H-WT means human wild type; M-WT means mouse wild type; Phe587Ala, human means Phe587Ala mutant.

FIG. 11 shows the purification profiles of recombinant μPlg with Superdex 200 SEC column chromatography and SP-Sepharose cation exchange chromatography. As described previously, the *E. coli* expressed inclusion bodies were purified, refolded and the refolded proteins were first purified using the Superdex 200 column (FIGS. 11*a*, 11*b* and 11*c*) and the second peaks (refolded peaks, red arrows) were further purified using SP XL columns (FIGS. 11*d*, 11*e* and 11*f*). Further, the purified μPlg were activated with SAK and the activated μPlm were also purified using SP XL columns (FIGS. 11*g*, 11*h* and 11*i*).

Figure 12:
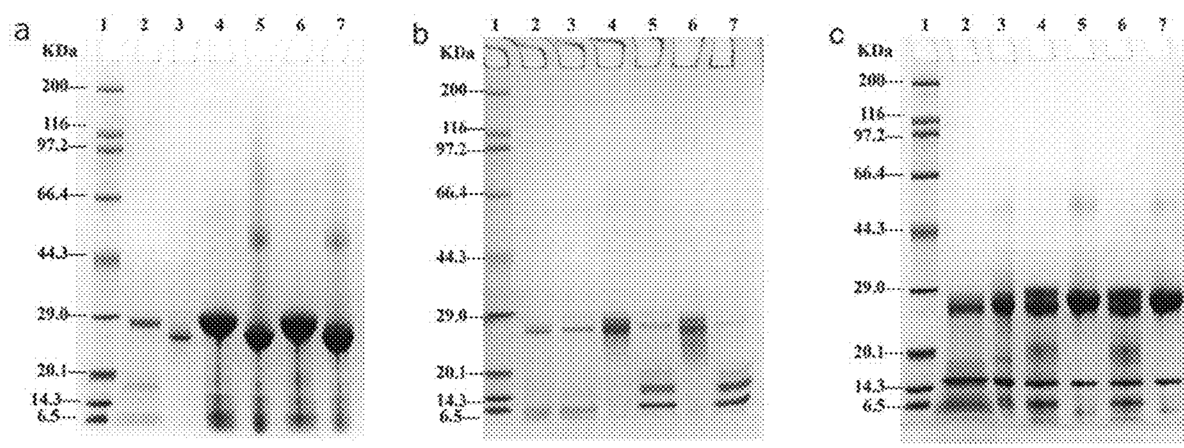
FIG. 12 shows SDS-PAGE of purified μPlg and μPlm variants, wherein (a) μPlg purification by superdex 200, wherein 1: marker, 2: M-WT reducing loading buffer, 3: M-WT non-reducing buffer, 4: H-WT reducing loading buffer, 5: H-WT non-reducing buffer, 6: H1-Phe587Ala reducing loading buffer, 7: H-Phe587Ala non-reducing buffer; (b) μPlg purification by SP XL, wherein 1: Marker, 2: M-WT non-reducing buffer, 3: M-WT reducing loading buffer, 4: H-WT non-reducing buffer, 5: H-WT reducing loading buffer, 6: H-Phe587Ala non-reducing buffer, 7: H-Phe587Ala reducing loading buffer; (c) μPlm purification by SP XL, wherein 1: marker, 2: M-WT reducing loading buffer, 3: M-WT means non-reducing buffer, 4: H-WT reducing loading buffer, 5: H-WT non-reducing buffer, 6: H-Phe587Ala reducing loading buffer, 7: H-Phe587Ala non-reducing buffer.
Figure 13:
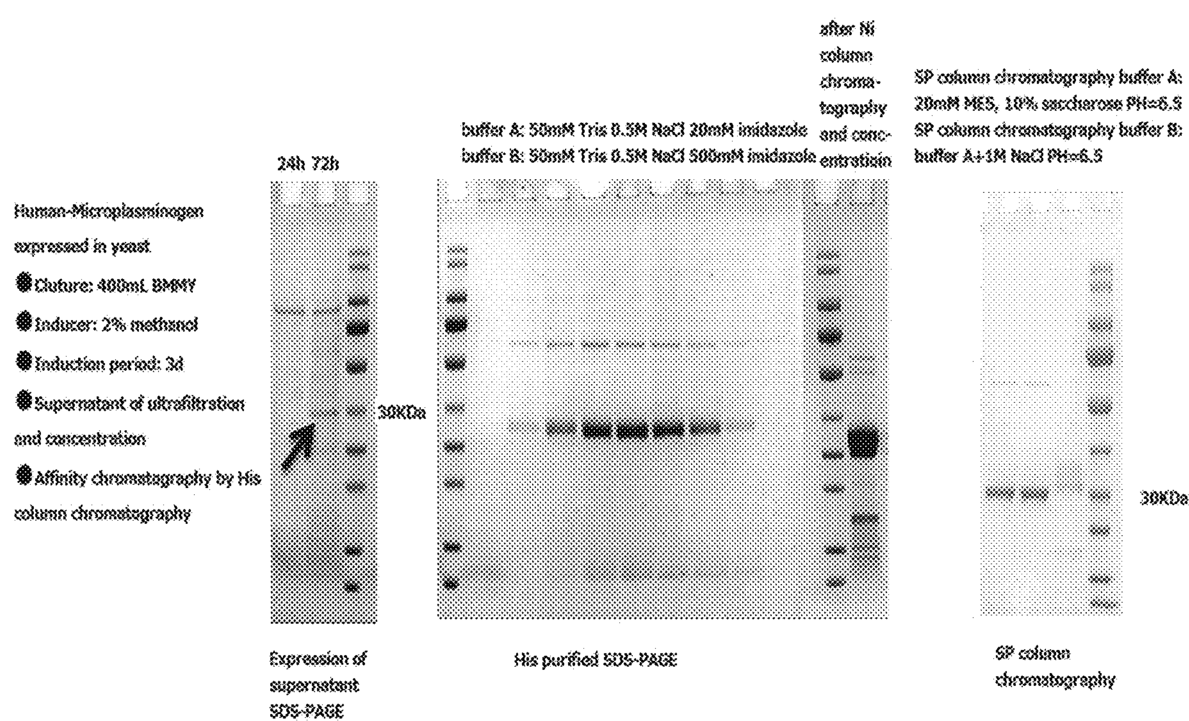
FIG. 13 shows Yeast expression and purification of human μPlg.

FIG. 12 shows SDS-PAGE of the column chromatography purified samples. FIG. 12*a* shows the purity of μPlg purified by Superdex 200 columns. Lanes 2, 4, 6 are reduced gel and 3, 5, 7 are non-reduced. The non-reduced SDS-PAGE showed a lower molecular weight because of the disulfide bonds in the protein molecules are all intact and the "tethered" molecules are smaller in shape than the extended, reduced conformation. FIG. 12*b* showed the purity of the SP XL column purified Plg. In this case, the reduced SDS-PAGE in lanes 5 and 7 showed smaller molecular weight, which is activated μPlg. The SDS-PAGE clearly showed that the *E. coli* refolded μPlg autoactivated to Plm during the purification process with the SP XL cation exchange column chromatography. The yeast expressed μPlg, on the other hand, is more stable and showed no autoactivation during the same purification process (FIG. 13). FIG. 12 shows the purification of yeast expressed M-μPlg (MY-μPlg). FIG. 13 shows the purification of yeast expressed H-μPlg (HY-μPlg).

Figure 14:
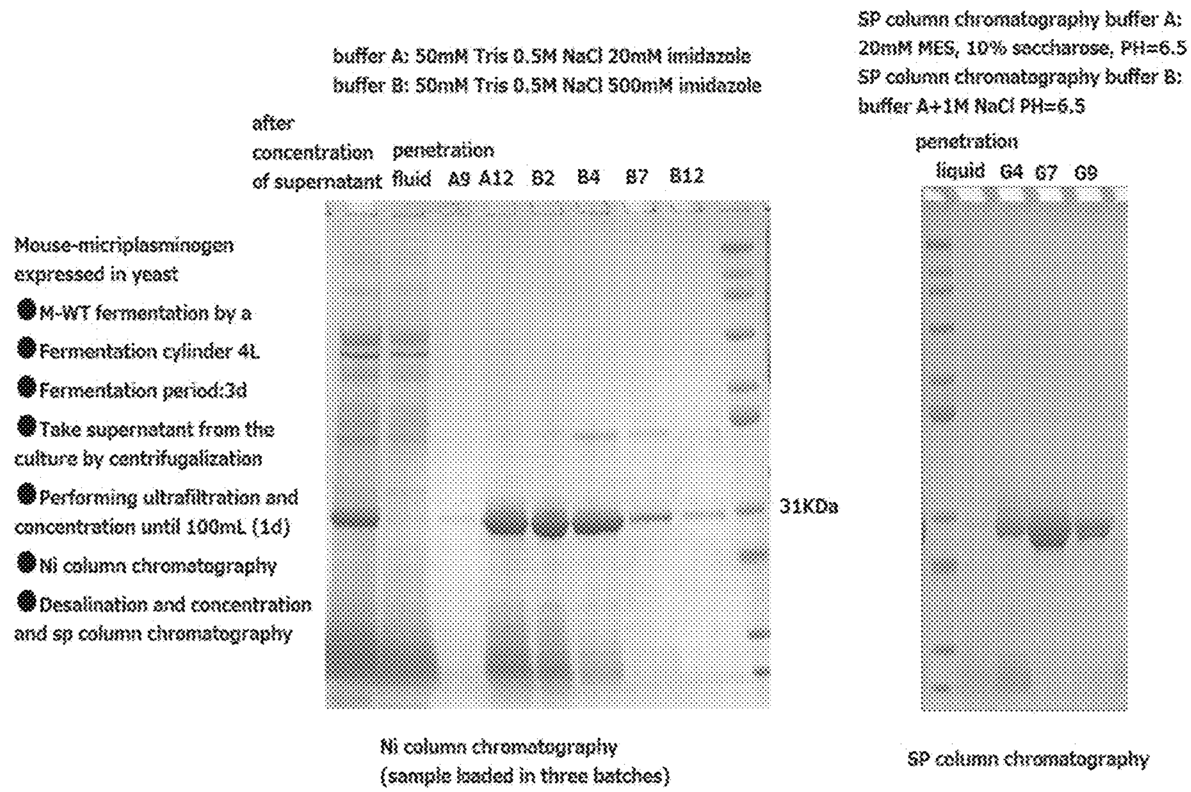
FIG. 14 shows Yeast expression and purification of mouse μPlg.

FIG. 14 shows the purification of yeast expressed M-μPlg (MY-μPlg). The *Pichia* yeast expressed μPlgs were first purified by affinity chromatography ($Ni^{+}$-affinity column), took advantage of the His-tag installed at the N-terminal of the recombinant proteins. The affinity purified proteins were than further purified using SP XL columns.

Synthetic genes of wild-type and mutant human and mouse μPlg optimized for *E. coli* expression was the same as previously published (PMID: 17126563 DOI: 10.1016/j.pep.2006.10.012) (PMID: 32694536 PMCID: PMC7374754 DOI: 10.1038/s41598-020-69079-8). Procedures for *E. coli* expression, inclusion body purification, refolding and purification were also the same as described in our previous publications (PMID: 32694536 PMCID: PMC7374754 DOI: 10.1038/s41598-020-69079-8). The initially purified Plg was further purified by a SP-Sepharose column chromatography.

Example II. Homology Modeling and Molecular Dynamics Simulation

To model the plasmin: α2-AP complex, the inventor of the present disclosure used the Protein PDB structures of 1BML (μPlm) and 2R9Y (α2-AP) (Law R H P, Sofian T, Kan W-T, Horvath A J, Hitchen C R, Langendorf C G, Buckle A M, Whisstock J C, Coughlin P B (2008) X-ray crystal structure of the fibrinolysis inhibitor α2-antiplasmin. Blood 111, 2049-2052). As shown in FIG. 2, these two structures are superimposed to the crystal structure of Trypsin: antiTrypsin complex (PDB ID: 1OPH) (Dementiev A, Simonovic M, Volz K, Gettins P G W (2003) *Canonical Inhibitor-like Interactions Explain Reactivity of* α1-*Proteinase Inhibitor Pittsburgh and Antithrombin with Proteinases. Journal of Biological Chemistry* 278, 37881-37887) to form the complex. As shown in FIG. 3, The crystal structure of 2R9Y misses the C-terminal residues, therefore the inventor of the present disclosure use I-TASSER server (Yang J, Zhang Y (2015) *I-TASSER server: new development for protein structure and function predictions. Nucleic Acids Research* 43, W174-W181) to build the missing residues. The protein complex was solvated in a rhombic dodecahedron solvent box with TIP3P (Jorgensen W L, Chandrasekhar J, Madura J D, Impey R W; Klein M L (1983) *Comparison of simple potential functions for simulating liquid water. The Journal of Chemical Physics* 79, 926-935) water molecule layer extended approximately 10 Å away from the surface of the proteins. Counter ions ($K^{+}$ and $Cl^{-}$) were added to ensure electrostatic neutrality corresponding to an ionic concentration of about 150 mM. As shown in FIG. 4, All protein covalent H-bonds were constrained with the LINCS (Hess B, Bekker H, Berendsen H J C, Fraaije JGEM (1997) *LINCS: A linear constraint solver for molecular simulations. J. Comput. Chem.* 18, 1463-1472) algorithm. And long-range electrostatic interactions are treated with the particle-mesh Ewald (Hess B, Bekker H, Berendsen H J C, Fraaije JGEM (1997) *LINCS: A linear constraint solver for molecular simulations. J. Comput. Chem.* 18, 1463-1472) method with a real-space cutoff of 10 Å. Parallel simulations are performed simultaneously.

Figure 15:
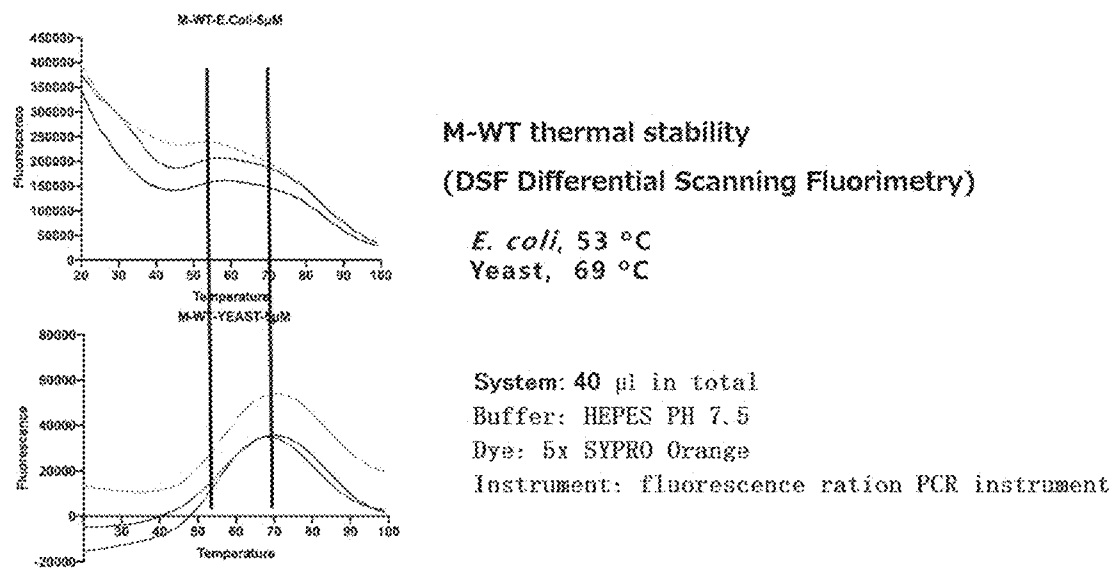
FIG. 15 shows the thermal Stability of *E. coli* and Yeast expressed mouse wild-type μPlg. The figure shows that the melting temperature of the *E. coli* refolded μPlg is 53° C. and the yeast expressed μPlg is 69° C. The difference of 16° C. reflected that the *E. coli* expressed and refolded Plg is much less stable than the yeast expressed, "natively folded" μPlg.

Example III. Measurement of Thermal Stability of *E. coli* and Yeast Expressed μPlg A fluorescence-based thermal denaturation assay (Differential Scanning Fluorimetry, DSF) was used to measure thermal stability (https://doi.org/10.1038/nprot.2007.321). The measurement was performed by using PCR tubes in a Bio-Rad CFX96 Real-Time PCR system (USA). A typical 40 μl reaction mixture contains SYPRO Orange 5X dye (from Thermo Fisher Scientific), 2.5 μM, 5 μM and 10 μM μPlg respectively, in 20 mM HEPES buffer, pH 7.5. The reaction plate was incubated at 25° C. for 30 min and then heated to 100° C. at 0.5° C. intervals, with a settling time for 30 seconds. The "Scan mode" was set to "FRET" and the fluorescence counts were plotted against temperature. Fluorescence was measured with excitation at 470 nm and emission at 570 nm. FIG. 15 shows the measured thermostability of *E. coli* and Yeast expressed μPlg. The figure shows that the melting temperature of the *E. coli* refolded μPlg is 53° C. and the yeast expressed μPlg is 69° C. The difference of 16° C. reflected that the *E. coli* expressed and refolded μPlg is much less stable than the yeast expressed, "natively folded" μPlg. The results support that the *E. coli* expressed and refolded μPlg is closer to be the "ideal" thrombolytic drug.

Figure 16:
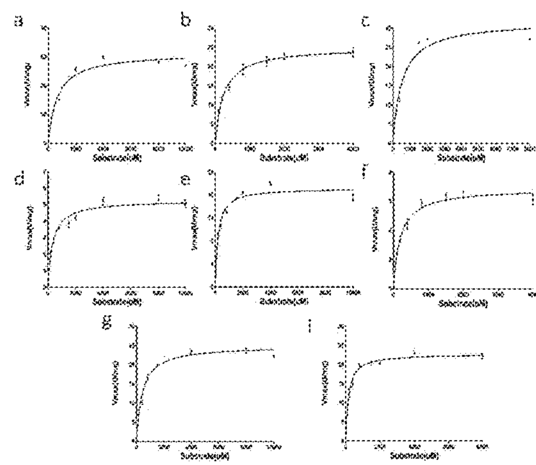
FIG. 16 shows the standard Michaelis-Menten kinetic measurements of purified recombinant μPlg and μPlm from *E. coli* and yeast. The figure shows that the kinetic parameters of the yeast expressed μPlg is different from the *E. coli* expressed μPlg and μPlm.

Example IV. Activation and Kinetic Measurements of *E. coli* and Yeast Expressed μPlg The kinetic measurements were essentially the same as described previously. Chromogenic substrate pGlu-Phe-Lys-pNA (S-2403) was used to monitor the proteolytic activity and 4-Nitrophenyl 4-guanidinobenzoate hydrochloride (pNPGB) was used to titer the active site of μPlm. Briefly, recombinant μPlg zymogens (35.5 μM) were activated with a plasminogen activator such as SK (20:1) at 37° C. for 10 min in a reaction mixture containing 25 mM Tris-HCl, pH 7.4, 50 mM NaCl. The active site of the activated Plm was titrated using pNPGB as described. The activated zymogens were diluted to 5.5 μM and then 10 μl was mixed with 100 μl of 0.0625 mM, 0.125 mM, 0.25 mM, 0.5 mM, 0.75 mM, 1.0 mM, 1.5 mM or 2.0 mM of substrate S-2403 in the assay buffer (25 mM Tris-HCl, 50 mM NaCl, pH 7.4). The generation of amidolytic activity was monitored (at 405 nm) at 37° C. in 10 second intervals for 20 min using a microplate reader from Thermo Fisher. The data was plotted as velocity vs. substrate using GraFit version 7 (Erithacus Software) and the Vmax and Km of the wild-type and each mutant μPlm were determined. The catalytic efficiency (Kcat/Km) was calculated according to the active enzyme concentration. The inventor of the present disclosure performed standard Michaelis-Menten kinetic measurements for human and mouse μPlm expressed in *E. coli* and yeast, shown in FIG. 16. The figure shows that the kinetic parameters of the yeast expressed μPlg is different from the *E. coli* expressed μPlg and μPlm, and taken together with results shown in FIG. 15, the *E. coli* expressed μPlm is more suitable for thrombolytic drug development.

Example V. Animal Test

Our animal studies of several versions of the μPlm indicated that not only the recombinant enzyme can resolve blood clots caused fatal disease in a mouse model of pulmonary embolism model, but also possessed minimum bleeding side effect in the therapeutic concentrations. The results may indicate that a long-standing problem facing thrombolytic drug development, which is the often-fatal bleeding side effect, can be avoided using recombinant μPlm described in the present disclosure. Contrary to the conventional approach of developing more stable, longer in vivo half-life thrombolytic therapeutics, results of the present disclosure support a new "hit and die" strategy, in which an "ideal" thrombolytic drug hits the targeting thrombi, dissolving them and die out, avoiding bleeding side effect resulting from continued activity of the present thrombolytic drugs.

The inventor of the present disclosure designed mouse models for pulmonary embolism, including a control group, a Sham operation group and a model group. KM mice (4-6 weeks old, weight about 36-47 g, Male (M) and Female (F) 1:1, n=8 each group) were purchased from Beijing Vital River Laboratory Animal Technology Co., Ltd., China. All experimental procedures were approved by the animal ethics committee and followed the Guide for the Care and Use of Laboratory animals of College of Life Science, South-Central University for Nationalities, Hubei, China.

The normal concentration of α2-AP in the blood is about 1 μM to neutralize active Plm in the blood to avoid toxic effect of the enzyme. In an animal test, the inventor of the present disclosure used 5-20 μM of μPlm to rescue mice in a mouse pulmonary embolism model. At this concentration of μPlm, all of the α2-AP would be neutralized and the active μPlm concentration in the blood would be 4-19 μM, which would kill animals by dissolving hemostatic plugs and causing excessive bleeding. But experimental results of the present disclosure showed that in the mouse model, the untreated animals dead from blood clotting and μPlm treated animals all survived without serious bleeding side effect. These results lead the inventor of the present disclosure to assume that after dissolving the freshly formed clots in the blood, the recombinant μPlm lost activity because of in vivo unstable and short half-life, avoided fatal bleeding side effect.

Then inventor of the present application provides preparation method for paraffin sections of the mouse tissue from each animal model by the following steps:

(1) Fixation: fixing 24 hours with paraformaldehyde.

(2) Washing and dehydration: from low to high ethanol concentration: 50%, 70%, 85%, 95%, 100%, incubate 1 hour at each concentration.

(3) Lucency: soak in n-butanol:ethanol=1:1 for 1 hour, then transfer to pure n-butanol for 1 hour.

(4) Waxing and embedding: in an incubator of temperature 3° C. higher than paraffin wax, put the lung lobe of mouse into melted wax/xylene (1:1) and incubate for 1 h, then move to melted wax and incubate for additional 3 h, twice. Pour melted paraffin into paraffin block mold. Place the tissue well in the mold and wait for its cooling down. (15-20 min)

(5) Slicing: section the paraffin-embedded tissue block in 4-10 μm thickness slides on a microtome and float in a 37° C. water bath containing deionized water.

(6) Paster and baking: Float the sections onto clean glass slides and microwave at 45° C. for 15 min, then the tissue binds to the glass and then incubate in a 45° C. incubator to dry.

(7) Dewaxing and hydration of slides: dewaxing in xylene and then step-by-step of changing to pure ethanol and pure water.

(8) Staining: the Hematoxylin and Eosin staining method is the common method in histological specimen staining, called HE staining. After HE stain, the cell nucleus are stained into violet blue and most of the cytoplasm and non-cellular component are stained into rose hermosa color.

Figure 10:
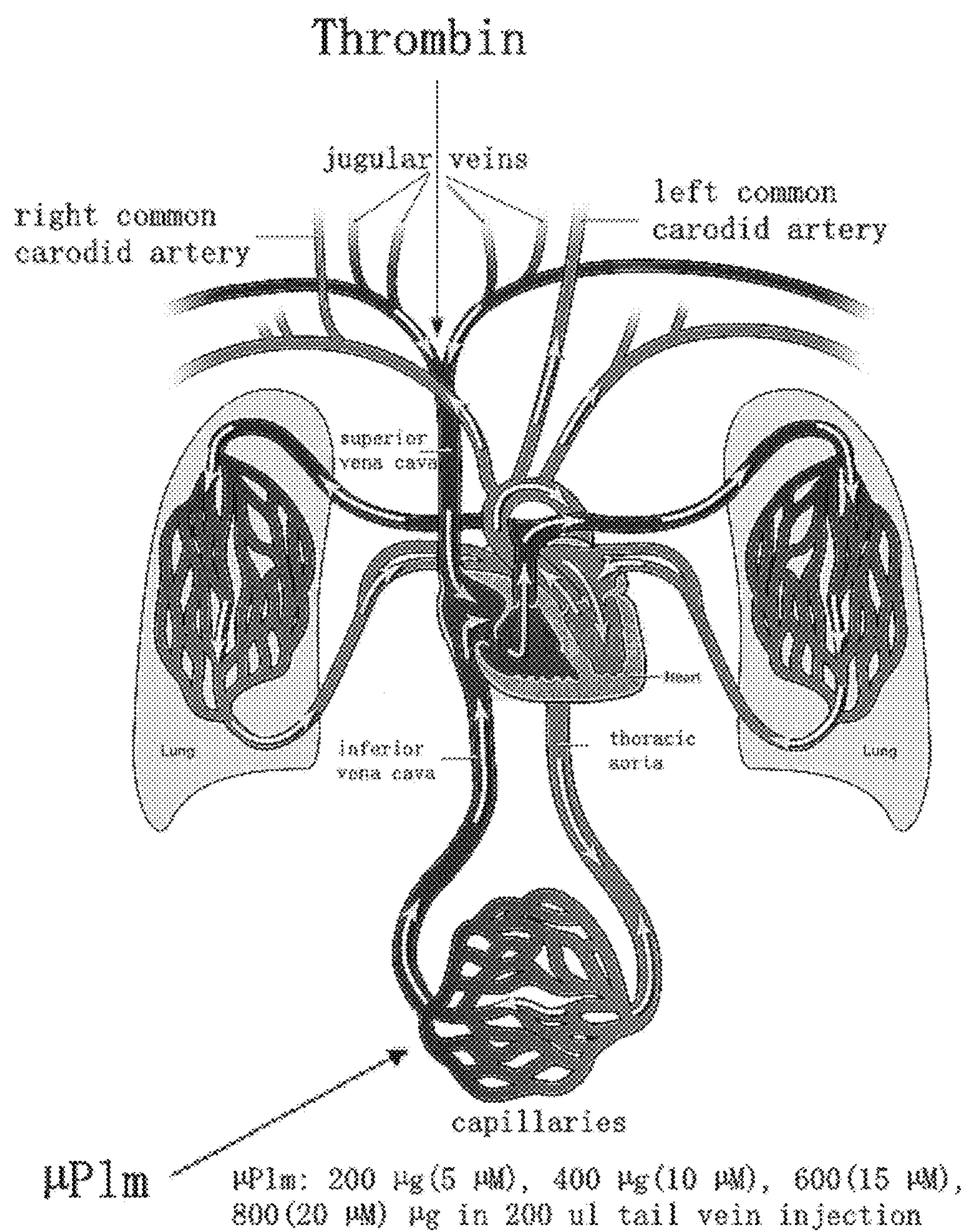
FIG. 10 shows the schematic presentation of the half-life experiment by tail intravenous injection and eye blood sampling at different time after the lethal and "therapeutical" test is performed on the mouse to observe its death and dissection.

The inventor of the present disclosure provide detail information about the mouse pulmonary embolism model (https://doi.org/10.1016/j.ddmod.2011.03.006), which is shown in FIG. 10. Animals were anesthetized with 20% urethane in the amount of 1.5 g/KG intraperitoneal injection and thrombin (20 U/kg) was injected through the internal jugular vein. After the neck incision was sutured, mice without treatment would die in 10-20 min resulting from thrombin-induced rapid blood clotting of the lungs and heart. The μPlm enzyme samples (100 μl each injection) were injected into the tail-vein 5 min after the application of thrombin. Survived mice were sacrificed in 24 hours and lung and heart tissues were fixed with 4% poly formaldehyde solution and paraffin embedded. Tissue sections were prepared by a specialized biotech company Biofavor Biotech Service Co., LTD. For measuring the in vivo half-life, the inventor of the present disclosure injected 100 μL of each μPlm enzyme diluted with PBS into the tail veins. The ocular bloods were collected at indicated times, samples were collected into 1 ml centrifuge tubes with anticoagulant and the resulting plasma were used to measure μPlm enzyme activity.

Figure 17:
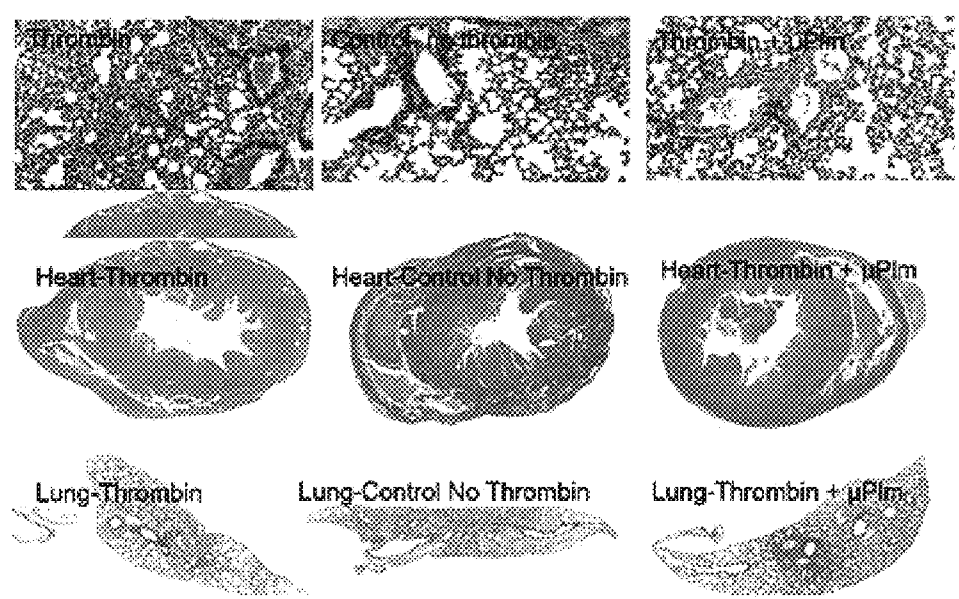
FIG. 17 shows the paraffin section of test mice tissue, wherein top panel, lung slide, thrombin causes blood clots, but μPlm dissolved the clots, wherein middle Panel, mouse dead of clotting by thrombin injection, no blood in the heart Lower Panel, mouse dead of clotting by thrombin injection, little blood in the lung.
Figure 18:
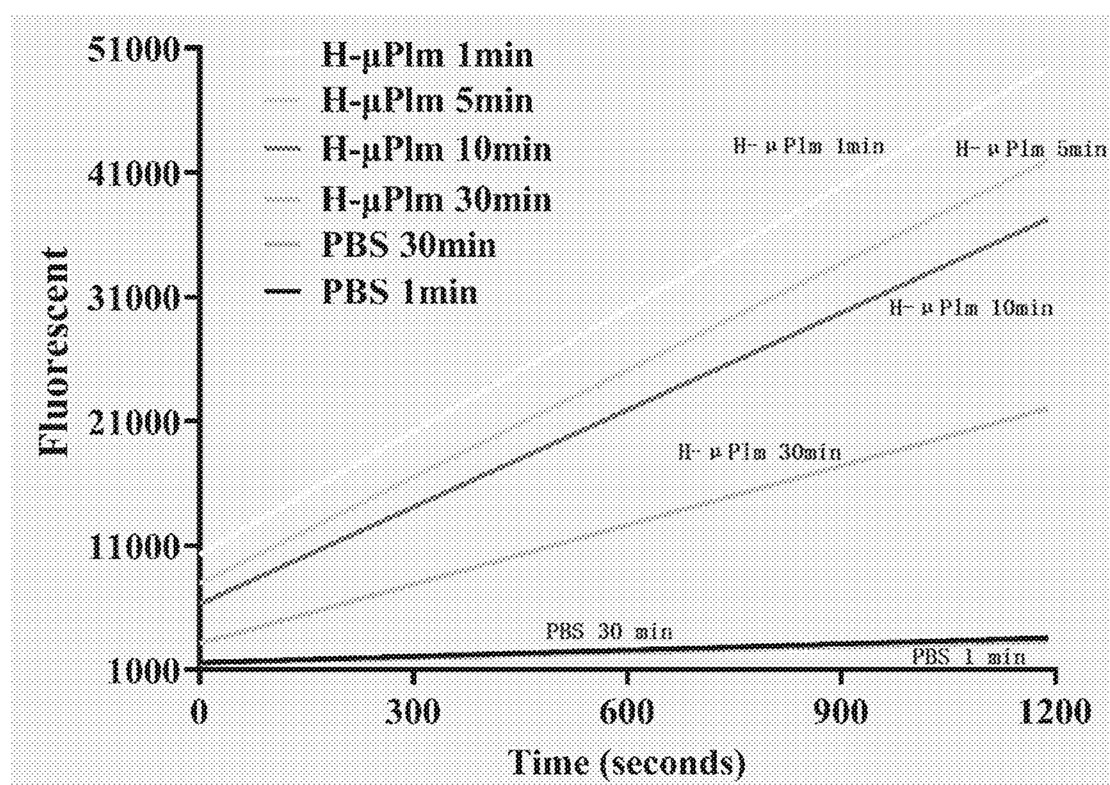
FIG. 18 shows the measurement for the in vivo half-life of the recombinant μPlm Phe587Ala, wherein H-μPlm represents human Phe587Ala, PBS: phosphate-buffered saline, control.
Figure 19:
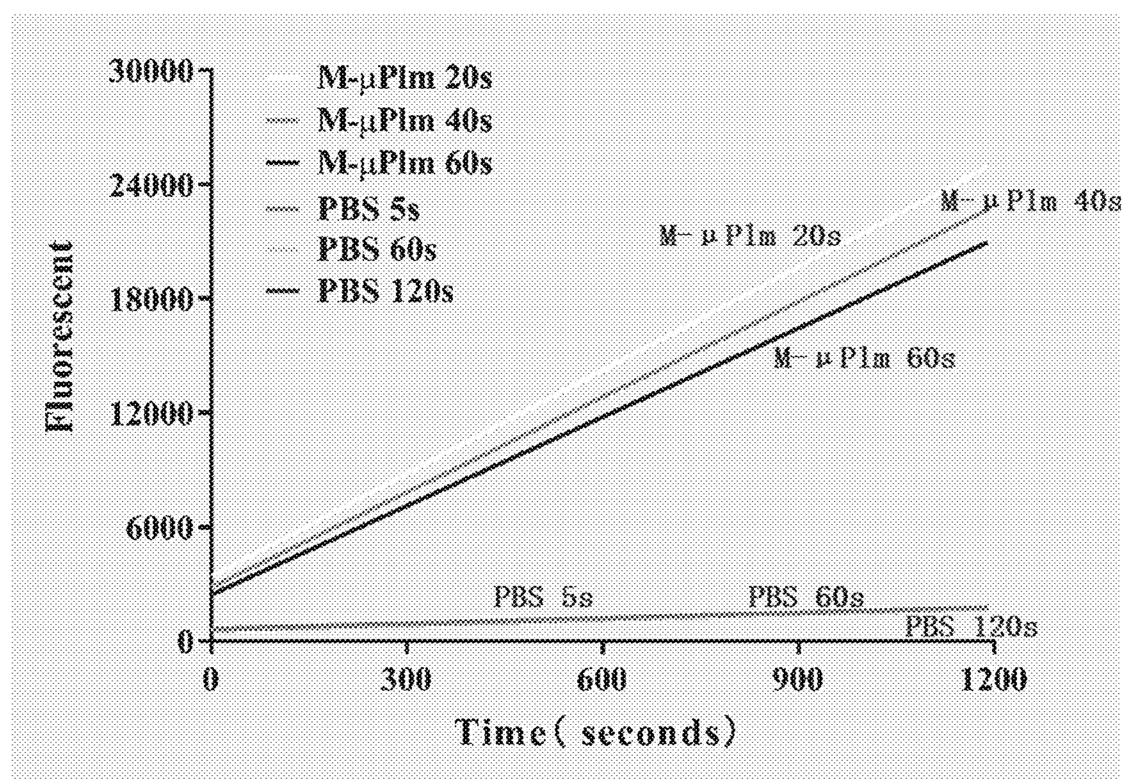
FIG. 19 shows the measurement for the in vivo half-life of the recombinant wild-type mouse μPlm, wherein M-μPlm represents mouse wild-type, PBS: phosphate-buffered saline, control.

The present disclosure further provides the issue section of the treated mouse dead from pulmonary embolism in FIG. 17 and experimental data for the treated mouse dead from pulmonary embolism in table 2 and table 3.

TABLE 2

Experimental data for control group of test mice dead from thrombin in 10-17 min.

| Category | Fc03 | Mc02 | Fct01 | Mct01 |
|---|---|---|---|---|
| Weight/g | 42.2 | 42.9 | 36.6 | 45 |
| Urethane/μL | 300 | 400 | 300 | 400 |
| Thrombin/μL | 0 | 0 | 73 | 90 |
| Saline-Neck Vein/μL | 85 | 86 | 0 | 0 |
| Saline-Tail Vein/μL | 200 | 200 | 200 | 200 |
| Injection Time-Tail (min) | 5 | 5 | 5 | 5 |
| Death Time (min) | / | / | 17 | 10 |

TABLE 3

Experimental data for test group of test mice 5 mins after thrombin treatment, wherein μPlm injection saved the life of test mouse.

| Category | Mtμ01 | Ftμ01 | Mtμ02 | Ftμ02 | Mtμ03 | Ftμ03 |
|---|---|---|---|---|---|---|
| Weight/g | 47 | 36.1 | 40.9 | 42.8 | 47.1 | 34.5 |
| Urethane/μL | 300 | 300 | 300 | 300 | 400 | 300 |
| Thrombin/μL | 94 | 73 | 82 | 86 | 94 | 69 |
| μPlm/μL | 200 | 200 | 200 | 200 | 200 | 200 |
| Injection Time-Tail (min) | 5 | 5 | 5 | 5 | 5 | 5 |
| μPlm mg/mL | 1 | 1 | 2 | 2 | 3 | 3 |

Following conclusions can be made from the animal test:

1. μPlm (wild-type and Phe587Ala) can rescue mouse from pulmonary embolism.

2. High concentration of the μPlm (wild-type and Phe587Ala) did not cause fatal bleeding. The animals were alive and well after μPlm treatment, while the untreated animals were dead in about 10-20 min after thrombin treatment, caused by thrombin induced pulmonary embolism.

3. The in vivo half-life of Plm: about 3-29 minutes, much shorter than published half-life of other thrombolytic agents (7 hours to 2-3 days, Collen, D., E. B. Ong, and A. J. Johnson, *Human plasminogen: In vitro and in vivo evidence for the biological integrity of NH2-terminal glutamic acid plasminogen. Thrombosis Research.* 1975; 7(4): 515-529.).

Example VI. Half-Life Calculation of μPlm from Mice Plasma Samples

All activity assays were performed using a Plasmin Activity Assay Kit (BioVision Fluorometric Assay) according to manufacturer's instructions.

Standard Curve Preparation: Prepare working solution of 10 ng/μl Plasmin Enzyme by adding 198 μl of Plasmin Dilution Buffer to 2 μl of Plasmin Enzyme Standard working solution. Mix well by pipetting up and down. Add 0, 5, 10, 15, 20, and 25 μl of the Plasmin Enzyme working solution (10 ng/μl) into a series of wells in a 96-well plate to prepare 50, 100, 150, 200, and 250 ng/well of Plasmin Enzyme Standard solution. Next, adjusting the volume to 50 μl/well with Plasmin Assay Buffer, and performing enzyme assay with the fluorescent substrate to obtain a standard curve. For Plm enzyme assay, the standard curve calculation is respectively performed to obtain the H-Phe587Ala simulation curve, i.e. y=−0.5575x+32.272, wherein correlation coefficient $R^2$ is 0.9828, and the M-μPlm-Male simulation curve, i.e. y=−0.0632x+19.293, wherein correlation coefficient $R^2$ is 0.995.

Figure 20:
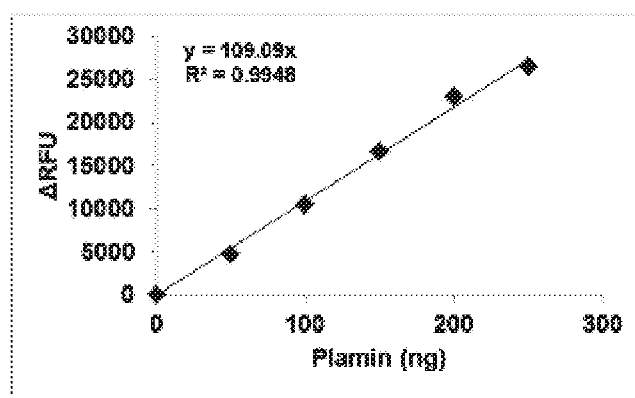
FIG. 20 shows the standard curve of ΔRFU versus the amount of standard Plm, wherein the curve is used to calculate the in vivo concentration of μPlm from measurements shown in FIG. 18 and FIG. 19.

Measurement: Measure fluorescence in kinetic mode for 10-20 min. at 37° C. (Ex/Em=360/450 nm). Choose two time points (T1=408 s and T2−=901 s) in the linear range of the plot and obtain the corresponding values for the fluorescence (ΔRFU (Relative Fluorescence Units)=RFU2−RFU1) to prepare H-Phe587Ala simulation standard curve of ΔRFU versus the amount of μPlm, i.e. y=109.09x, wherein correlation coefficient $R^2$ is 0.9948. For the simplification of experiment, M-μPlm-Male also adopts this simulation curve, as shown in FIG. 20, wherein if the sample background control reading is significant, subtract the sample background control reading from sample reading.

Calculations: Subtract background (or control) reading from all readings. Plot the Plasmin Standard Curve. Apply sample's ΔRFU to Plasmin Standard Curve to obtain corresponding Plasmin (B, in ng) and calculate the activity of Plasmin in the sample as:

$$\text{Sample Plasmin Activity}=B/V\cdot\text{Dilution Factor}=\text{ng/ml}=\mu\text{g/L}$$

Wherein B is μPlm amount from Standard Curve (ng) and V is the sample volume added into the reaction well (ml)

Figure 21:
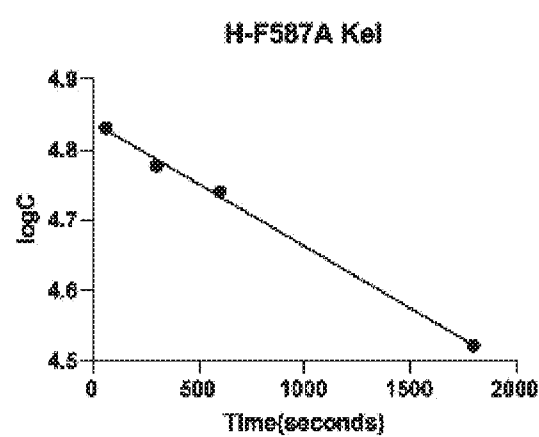
FIG. 21 shows the half-life calculation curve of human Phe587Ala, wherein the calculated value for the in vivo half-life of Phe587Ala is: $t_{1/2}$: 28.52±1.05 min.

In vivo half-life measurement system: 2 μL plasma+2 μL substrate+96 μL Assay Buffer Simulating the standard curve of log $C_t$ versus time, as shown in FIG. 21, to obtain the slope and finally obtain in vivo half-life of F587A as: $Ht_{1/2}$=28.52±1.05 min.

Figure 22:
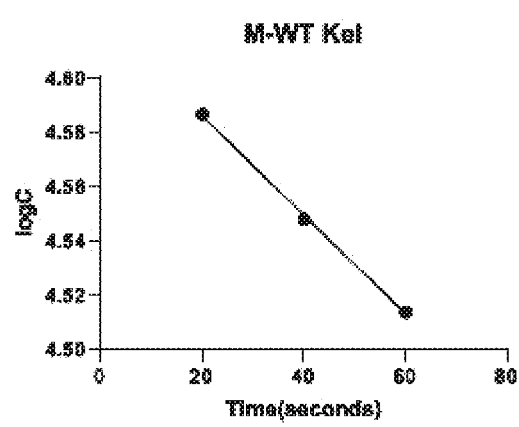
FIG. 22 shows the half-life calculation curve of mouse wild-type μPlm, wherein the calculated value for the in vivo half-life of mouse wild-type μPlm is: $t_{1/2}$: 2.75±0.09 min.

Simulating the standard curve of log $C_t$ versus time, as shown in FIG. 22, to obtain the slope and finally obtain in vivo half-life of mouse wild-type μPlm as: $Mt_{1/2}$=2.75±0.09 min.

The invention claimed is:

1. A short in vivo half-life and in vivo unstable recombinant microplasmin obtained by alanine scanning mutagenesis, wherein the recombinant microplasmin is obtained by expressing in a bacteria host, or refolding and purifying when the recombinant microplasmin is expressed as an insoluble inclusion body, the in vivo half-life of the recombinant microplasmin is about 2.75 to about 28.5 minutes;

wherein the short in vivo half-life and in vivo unstable recombinant microplasmin includes at least one of wild-type, Gly739Ala, Arg582Ala, Met585Ala, Lys607Ala, Phe587Ala, Ser608Ala, Arg610Ala, Glu641Ala, Pro642Ala.

2. The short in vivo half-life and in vivo unstable recombinant microplasmin of claim 1, wherein the recombinant microplasmin includes a wild type and a mutant type.

3. The short in vivo half-life and in vivo unstable recombinant microplasmin of claim 1, wherein the recombinant microplasmin includes a human and a mouse microplasmin.

4. The short in vivo half-life and in vivo unstable recombinant microplasmin of claim 1, wherein the recombinant microplasmin is expressed and purified from an *E. coli* expression system.

5. The short in vivo half-life and in vivo unstable recombinant microplasmin of claim 1, wherein the recombinant microplasmin is biologically active in cleaving and detoxifying a pathogenic polypeptide or insoluble fibrin and is also resisting α2-antiplasmin inhibition, wherein the pathogenic polypeptide includes polypeptides causing cardiovascular diseases, Alzheimer's Disease, pulmonary fibrosis and COVID-19 caused systematic thrombosis.

6. A pharmaceutical composition comprising the short in vivo half-life and in vivo unstable recombinant microplasmin of claim 1 as a thrombolytic agent, or a pharmaceutically acceptable dosage form thereof, or a pharmaceutically acceptable solvate of the pharmaceutical composition or dosage form, and including a pharmaceutically acceptable excipient.

7. The pharmaceutical composition of claim 6, wherein the recombinant microplasmin is refolded and purified into an active form for thrombolytic applications.

* * * * *